(12) United States Patent
Morgan et al.

(10) Patent No.: US 12,072,274 B2
(45) Date of Patent: Aug. 27, 2024

(54) IMPEDANCE FLOW CYTOMETRY METHODS

(71) Applicants: University of Southampton, Southampton (GB); The University of Western Australia, Crawley (AU)

(72) Inventors: Hywel Morgan, Southampton (GB); Daniel Spencer, Southampton (GB); Timothy John Jay Inglis, Crawley (AU); Teagan Paton, Perth (AU); Kieran Mulroney, Perth (AU)

(73) Assignees: University of Southampton, Southampton (GB); The University of Western Australia, Crawley (AU)

(*) Notice: Subject to any disclaimer, the term of this patent is extended or adjusted under 35 U.S.C. 154(b) by 627 days.

(21) Appl. No.: 17/276,717

(22) PCT Filed: Sep. 16, 2019

(86) PCT No.: PCT/GB2019/052593
§ 371 (c)(1),
(2) Date: Mar. 16, 2021

(87) PCT Pub. No.: WO2020/058682
PCT Pub. Date: Mar. 26, 2020

(65) Prior Publication Data
US 2022/0034781 A1 Feb. 3, 2022

(30) Foreign Application Priority Data
Sep. 17, 2018 (GB) .................................... 1815122

(51) Int. Cl.
*G01N 15/12* (2024.01)
*C12Q 1/18* (2006.01)
(Continued)

(52) U.S. Cl.
CPC ............... *G01N 15/12* (2013.01); *C12Q 1/18* (2013.01); *G01N 15/0227* (2013.01);
(Continued)

(58) Field of Classification Search
CPC ............... G01N 15/12; G01N 15/0227; G01N 15/1031; G01N 15/1056;
(Continued)

(56) References Cited

U.S. PATENT DOCUMENTS 4,246,343 A * 1/1981 Wilkins ................ C12Q 1/18
435/38
2014/0199703 A1* 7/2014 Azevedo Pina Vaz .. C12Q 1/04
435/6.15
(Continued)

FOREIGN PATENT DOCUMENTS

EP 2259044 12/2010
EP 3266878 1/2018
(Continued)

OTHER PUBLICATIONS

Di Berardino, Marco et al., "Impedance Microflow Cytometry for Viability Studies of Microorganims", Proc. of SPIE, vol. 7902, pp. 790212-1 to 790212-7, 2011.*
(Continued)

*Primary Examiner* — Helen C Kwok
(74) *Attorney, Agent, or Firm* — Renner, Otto, Boisselle & Sklar, LLP

(57) ABSTRACT

A method of antimicrobial susceptibility testing comprises: preparing samples of microorganisms suspended in an electrolyte, comprising a first sample of the microorganisms unexposed to antimicrobial agents and a second sample of the microorganisms exposed to an antimicrobial agent; passing the first sample through an impedance flow cytometer to obtain a first impedance signal representing one or
(Continued)

more components of impedance values of the unexposed microorganisms; passing the second sample through the impedance flow cytometer to obtain a second impedance signal representing one or more components of the impedance values of the exposed microorganisms; comparing the first impedance signal and the second impedance signal; and determining a susceptibility of the microorganisms to the antimicrobial agent based on any differences between the first impedance signal and second impedance signal.

15 Claims, 14 Drawing Sheets

(51) Int. Cl.
 *G01N 15/02* (2024.01)
 *G01N 15/0227* (2024.01)
 *G01N 15/10* (2024.01)
 *G01N 15/1031* (2024.01)

(52) U.S. Cl.
 CPC ..... *G01N 15/1023* (2024.01); *G01N 15/1031* (2013.01); *G01N 2015/0294* (2013.01); *G01N 2015/1006* (2013.01); *G01N 2015/1029* (2024.01); *G01N 2015/103* (2024.01)

(58) Field of Classification Search
 CPC ... G01N 2015/1006; G01N 2015/1087; G01N 15/0294; G01N 2015/1093; C12Q 1/18
 See application file for complete search history.

(56) References Cited

U.S. PATENT DOCUMENTS

| | | | |
|---|---|---|---|
| 2016/0041080 A1* | 2/2016 | Spencer | G01N 15/1031 73/61.71 |
| 2017/0067840 A1* | 3/2017 | Kilian | C12Q 1/04 |
| 2017/0298456 A1 | 10/2017 | Holder et al. | |
| 2018/0051311 A1* | 2/2018 | Ekinci | G01N 33/48735 |
| 2018/0335405 A1* | 11/2018 | Shih | G01N 29/036 |
| 2019/0352693 A1* | 11/2019 | Ramjeet | G01N 21/6428 |
| 2021/0331166 A1* | 10/2021 | D'Amico | B01L 3/502761 |
| 2022/0340951 A1* | 10/2022 | Corrigan | G01N 27/122 |
| 2023/0140713 A1* | 5/2023 | Sutton | C12Q 1/18 435/32 |

FOREIGN PATENT DOCUMENTS

| | | |
|---|---|---|
| WO | 2012164547 | 12/2012 |
| WO | 2014170625 | 10/2014 |
| WO | 2014170626 | 10/2014 |
| WO | 2018132680 | 7/2018 |
| WO | 2018184073 | 10/2018 |
| WO | 2019012501 | 1/2019 |

OTHER PUBLICATIONS

M.J. Pucci, et al., "Inhibition of beta-lactam antibiotics at two different times in the cell cycle of *Streptococcus faecium* ATCC 9790," Bacteriology 165 682-688, 1986.

International Search Report and Written Opinion for corresponding International Patent Application No. PCT/GB2019/052593, dated Jan. 27, 2020.

UK Search Report, issued in Application No. GB1815122.5, dated Mar. 15, 2019.

K. T. Mulroney, et al., "Rapid susceptibility profiling of carbapenem-resistant Klebsiella pneumoniae," Scientific Reports, vol. 7, No. 1, May 15, 2017 (May 15, 2017), pp. 1-13, XP055540312.

* cited by examiner

IMPEDANCE FLOW CYTOMETRY METHODS

This application is a national phase of International Application No. PCT/GB2019/052593, filed on Sep. 16, 2019, which claims priority to GB Application No. 1815122.5, filed on Sep. 17, 2018, all of which are hereby incorporated by reference.

BACKGROUND OF THE INVENTION

The present invention relates to methods of impedance flow cytometry, for example the use of impedance flow cytometry to determine antimicrobial susceptibility.

Antimicrobial resistance (AMR) is the ability of a microorganism to avoid, modify or adapt to the adverse effects of an antimicrobial agent used against it. Of particular concern is a rise in, and global spread of, resistant bacteria, which is now recognised as a leading threat to the health and wealth of the world's population. When an infection is suspected, a doctor often immediately prescribes antimicrobial agents with the aim of promptly providing effective treatment. However, in many cases the antimicrobial agents are either not needed, or are inappropriate for the particular infection-causing organism. One notable problem is treatment of bacterial infections with antimicrobial agents which are ineffective owing to the presence of resistance mechanisms. This can mean the infection may persist, increase in severity and possibly spread to other patients. A leading reason for the rapid prescribing of potentially ineffective antimicrobial agents is that laboratory tests for checking antimicrobial resistance traits are far too slow to be useful in informing antimicrobial prescribing when the patient initially presents for treatment.

Typically, antimicrobial susceptibility tests measure microbial growth in the presence of antimicrobial agents in liquid cultures or on solid agar plates. A common test known as a disk diffusion test (or quantitative variations of this test principle called Etests) requires that a microbial culture be grown overnight to obtain a sample which is then placed on an agar plate. Discs or strips containing known concentrations of antimicrobial agents are placed on the agar plate, and the inhibition of microbial growth close to the discs or strips containing antimicrobial agents is measured after a long incubation period. The broth microdilution method measures the growth of microorganisms in liquid cultures with different concentrations of antimicrobial agents to determine the antimicrobial concentration at which microbial growth is inhibited (known as the minimum inhibitory concentration, or MIC). The broth microdilution MIC method may be performed using automated laboratory equipment. These conventional assays measure the growth of populations of microorganisms over time and take many hours to perform. The results cannot therefore be used to inform or guide prescription in the early stages of infection, when that guidance is most important.

As an alternative to these conventional tests which measure populations of microorganisms, analysing the optical properties of single microorganisms exposed to antimicrobial agents has been demonstrated to correlate closely with the antimicrobial susceptibility measured with the conventional tests, but within a shorter time window of less than one hour [1]. Commonly, a population of microorganisms is exposed to an antimicrobial agent for a fixed duration of time, typically thirty minutes. The microorganisms are then washed by centrifugation to remove the antimicrobial agent, and stained with a specific membrane-permeable fluorescent dye that can be used to indicate susceptibility to the agent. The optical properties of the microorganisms are measured with an optical flow cytometer, which detects light scattered from the microorganisms in a forward direction that indicates particle size, and a fluorescence signal corresponding to microorganisms. The optical data are compared with data obtained from a population of the same sample of microorganism, also stained with dye but which has not been exposed to the antimicrobial agent. Differences in the data from the two samples indicate whether the microorganisms are susceptible to the agent. Additionally, exposure of samples to a series of different antimicrobial concentrations is used to determine a minimum dose of antimicrobial agent required to effectively inhibit the microbial growth. Optical cytometry has a number of drawbacks. The use of dyes typically requires one or more wash steps in the procedure, which limits the scope for miniaturising and automating the test procedure. Removal of the antimicrobial agent by washing prior to addition of the dye suspends the antimicrobial treatment at that moment, so preventing continuous measurements of antimicrobial effects on a single sample over time. Optical cytometers are bulky and very costly, and require manipulation techniques such as hydrodynamic and/or acoustic focusing to correctly position the microorganisms within an optical analysis zone. The fluorescent dyes are also expensive. Hence, optical cytometry is not well-suited for the analysis of antimicrobial susceptibility at the point of need.

New approaches able to increase the speed and reduce the cost of the analysis of antimicrobial susceptibility testing, and hence guide appropriate antimicrobial prescription, are therefore required.

SUMMARY OF THE INVENTION

Aspects and embodiments are set out in the appended claims.

According to a first aspect of certain embodiments described herein, there is provided a method of antimicrobial agent susceptibility testing comprising: preparing samples of microorganisms suspended in an electrolyte, comprising a first sample of the microorganisms unexposed to antimicrobial agents and a second sample of the microorganisms exposed to an antimicrobial agent; passing the first sample through an impedance flow cytometer to obtain a first impedance signal representing one or more components of impedance values of the unexposed microorganisms; passing the second sample through the impedance flow cytometer to obtain a second impedance signal representing one or more components of the impedance values of the exposed microorganisms; comparing the first impedance signal and the second impedance signal; and determining a susceptibility of the microorganisms to the antimicrobial agent based on any differences between the first impedance signal and second impedance signal.

According to a second aspect of certain embodiments described herein, there is provided a method of impedance flow cytometry comprising: flowing a sample of fluid comprising particles suspended in an electrolyte along a flow channel; applying electrical signals to current paths through the fluid, the current paths comprising at least a first current path, a second current path, a further first current path and a further second current path, wherein the electrical signals applied to the first current path and the further first current path have a frequency, magnitude and phase and the electrical signals applied to the second current path and the further second current path have substantially equal frequency and magnitude and opposite phase to the electrical signals applied to the first current path and the second current path; detecting current flow in the current paths; producing a first summed signal representing the sum of the current flow detected in the first current path and the second current path, and a second summed signal representing the sum of the current flow detected in the further first current path and the further second current path; and obtaining a differential signal representing the difference between the first summed signal and the second summed signal.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, methods may be provided in accordance with approaches described herein which includes any one or more of the various features described below as appropriate.

BRIEF DESCRIPTION OF THE DRAWINGS

For a better understanding of the invention and to show how it may be carried into effect, reference is now made by way of example to the accompanying drawings in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

Disc diffusion, broth microdilution and optical flow cytometry are examples of testing procedures for determining the susceptibility of microorganisms to antimicrobial agents. Such tests or assays can be termed antimicrobial susceptibility tests or testing (AST). The present disclosure proposes the use of an alternative procedure for this and other purposes using impedance flow cytometry. This technique uses apparatus to measure electrical properties, specifically a frequency dependent impedance, of individual particles flowing in a microfluidic channel. It has been found that exposure to antimicrobial agents (antimicrobials, antibiotics) can alter the impedance characteristics of a suspension of microorganisms (such as bacteria). The use of impedance flow cytometry to detect a change in the impedance of single microorganisms flowing through a microfluidic channel is proposed for the determination of susceptibility of the microorganisms to an antimicrobial agent under test.

For the purposes of the present disclosure, an antimicrobial or antimicrobial agent is considered to be any agent that kills or inhibits growth of one or more strains of microorganism. Examples of antimicrobials are antibiotics, antifungals and antivirals. Antibiotics are agents that kill (bactericidal), or inhibit growth of (bacteriostatic), bacteria. An Antibiotic may act by one of a number of different mechanisms including, but not limited to, disrupting synthesis or integrity of the microbial cell wall, blocking protein translation, preventing nucleic acid replication, repair or maintenance within the cell, preventing synthesis of essential molecules (e.g. folic acid, cholesterol) and perturbing membrane structure. Examples of classes of antibiotics are Aminoglycosides, Ansamycins, Azoles, Carbacephems, Carbapenems, Cephalosporins, Echinocandins, Glycopeptides, Lincosamides, Lipopeptides, Macrolides, Monobactams, Nitrofurans, Oxazolidinones, Penicillins, Pleuromutilin, Quinolones, Fluoroquinolones, Sulfonamides, Tetracyclines, and Trimethoprim, although other antibiotics and antimicrobials are not excluded. Cephlosporins, penicillins and carbapenems may be co-formulated with beta-lactamase inhibitors to improve efficiency.

For the purposes of the present disclosure, a microorganism is considered to be a microscopic organism, which may exist in its single-celled form or in a colony of cells. Examples of microorganisms include bacteria, virus and fungi (including yeasts and moulds).

Figure 1:
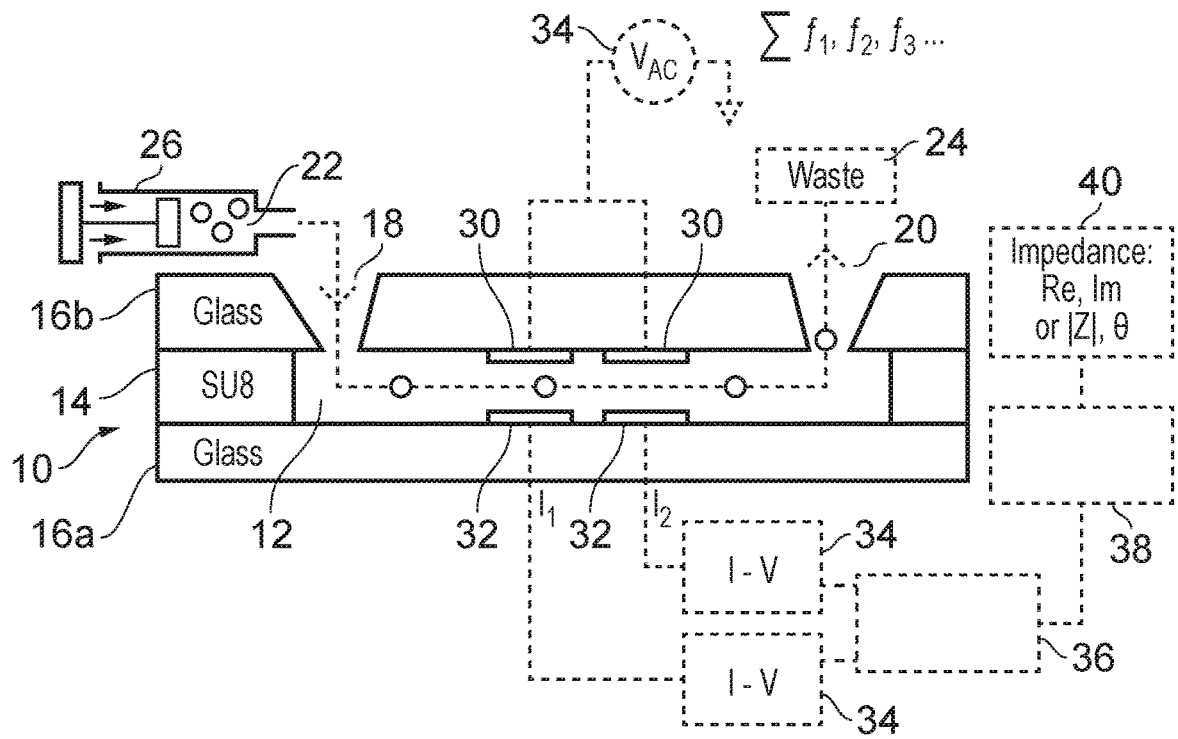
FIG. 1 shows a schematic cross-sectional side view of an example impedance flow cytometry apparatus.

FIG. 1 shows a simplified schematic cross-sectional side view of a first example of an apparatus for impedance flow cytometry, having a relatively simple format. The apparatus is typically constructed as a microfluidic device formed from various layers deposited on a substrate and patterned using techniques such as photolithography to form required structures. The field of microfluidics is concerned with the behaviour, control and manipulation of fluids which are confined or constrained on a small scale, typically sub-millimetre, in other words on the micro-millimetre or smaller scale. Microfluidic devices constructed from layers on a substrate for the purpose of sample testing, in the biological and medical fields as well as other areas of endeavour, are sometimes referred to as "lab-on-a-chip" devices. In the FIG. 1 example, the device 10 comprises a microfluidic flow channel 12 formed within a layer 14 of photoresist material, such as SU8, an epoxy-based negative photoresist, which is sandwiched between a lower layer 16a and an upper layer 16b of a glass material. Apertures in the upper glass layer 16a define an inlet 18 to the channel 12 and an outlet 20 from the channel 12. A fluid sample 22 can be delivered into the channel 12 at the inlet 18 for flow along the channel 12 (indicated by dotted arrows in FIG. 1) to the outlet 20 where it is removed or expelled as a waste product 24 or collected for further analysis. The sample 22 can be provided into the channel 12 by any convenient method, such as injection into the inlet 18 from a syringe 26. A sheath flow may or may not be used to centre particles within the bore or orifice of the channel. Other mechanisms may be used to focus particles in the flow such as dielectrophoresis, acoustic, inertial or viscoelastic techniques.

The sample 22 comprises particles, which may be cells, bacteria, microorganisms or other biological particles (such as algae, exosomes, viruses or vesicles) or non-biological particles (such as droplets, beads, colloids, dust or metal fragments), depending on the nature of the testing being carried out, suspended in an electrolyte (electrolytic fluid). For AST, the particles are microorganisms which have or have not been exposed to an antimicrobial agent. To accommodate the passage of cells, the channel may have a cross-section in the direction transverse to the flow direction (from inlet to outlet) measuring around 40 µm high and around 40 µm wide. More generally, channel dimensions might be in the range of 1 to 100 µm. The cross-section may or may not be square.

The device 10 further comprises a first and a second pair of electrodes fabricated on the bottom and top walls of the channel 12. Each pair of electrodes comprises a voltage electrode 30 and a measurement electrode 32. In the illustrated example of FIG. 1, the voltage electrode 30 is on the top wall of the channel 12 and the measurement electrode 32 is on the bottom wall of the channel 12, but these positions may be reversed. The first electrode pair is located at an upstream position in the channel 12, and the second electrode pair is located at a downstream position, so that particles in sample flow past the first electrode pair before the second electrode pair. The electrodes may have dimensions of the order 1 to 100 µm, such as 10 to 40 µm for analysing microorganisms and bacteria, although larger or smaller sizes are also possible depending on the channel size.

The voltage electrodes 30 are driven with a single voltage source 34 that may generate one or more frequency components $f_1$, $f_2$, $f_3$ . . . . Hence, both voltage electrodes 30 provide the same voltage, approximately equal in magnitude, frequency and phase. The two electrodes 30, 32 in each pair provide or define a current path across the flow channel 12 from the voltage electrode 30 to the measurement electrode 32, in the presence of the electrolytic fluid of a sample 22 flowing in the flow channel 12. Current flowing in these current paths is detected at the measurement electrodes 32. Current I1 detected at the first measurement electrode and current I2 detected at the second measurement electrode are each passed to a separate current-to-voltage converter 34. The outputs of converters are passed to a differential amplifier 36 to obtain a differential signal representing the difference between the currents in the two current paths, namely I2−I1 (or I1−I2 if preferred). Further electronics (circuitry, a lock-in amplifier 38, a processor 40, for example), receive the differential signal and determine from it a measurement of impedance. This output or impedance signal may separate the impedance measurements according to the real (Re) and Imaginary (Im) components, or the components of magnitude |Z| and phase θ, as preferred. Particles passing between the electrodes of an electrode pair will alter the current detected at the measurement electrode, which is reflected in the final impedance signal. Hence, the presence of a particle, and characteristics of the particle, may be deduced from the impedance signal.

The inclusion of two pairs of electrodes gives two measurable currents and enables the differential mode of operation noted above, to reduce noise and artefacts. The purpose of the differential signal can be understood with reference to FIGS. 2 and 3.

Figure 2:
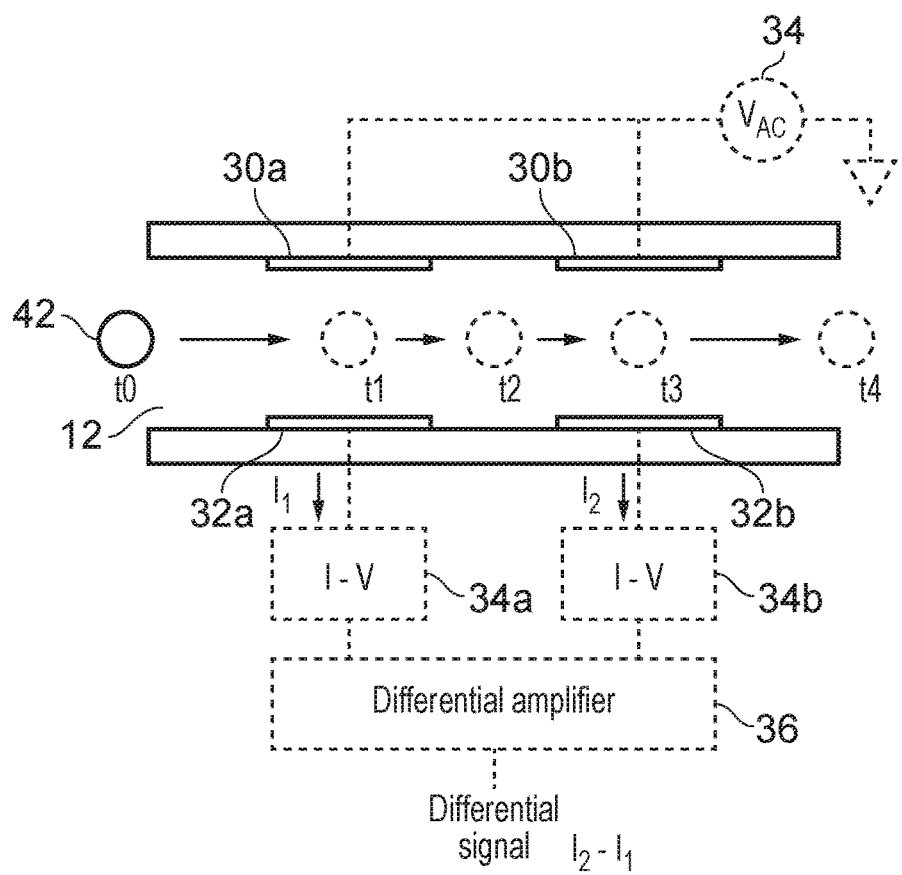
FIG. 2 shows a schematic cross-sectional side view of part of the apparatus of FIG. 1.
Figure 3:
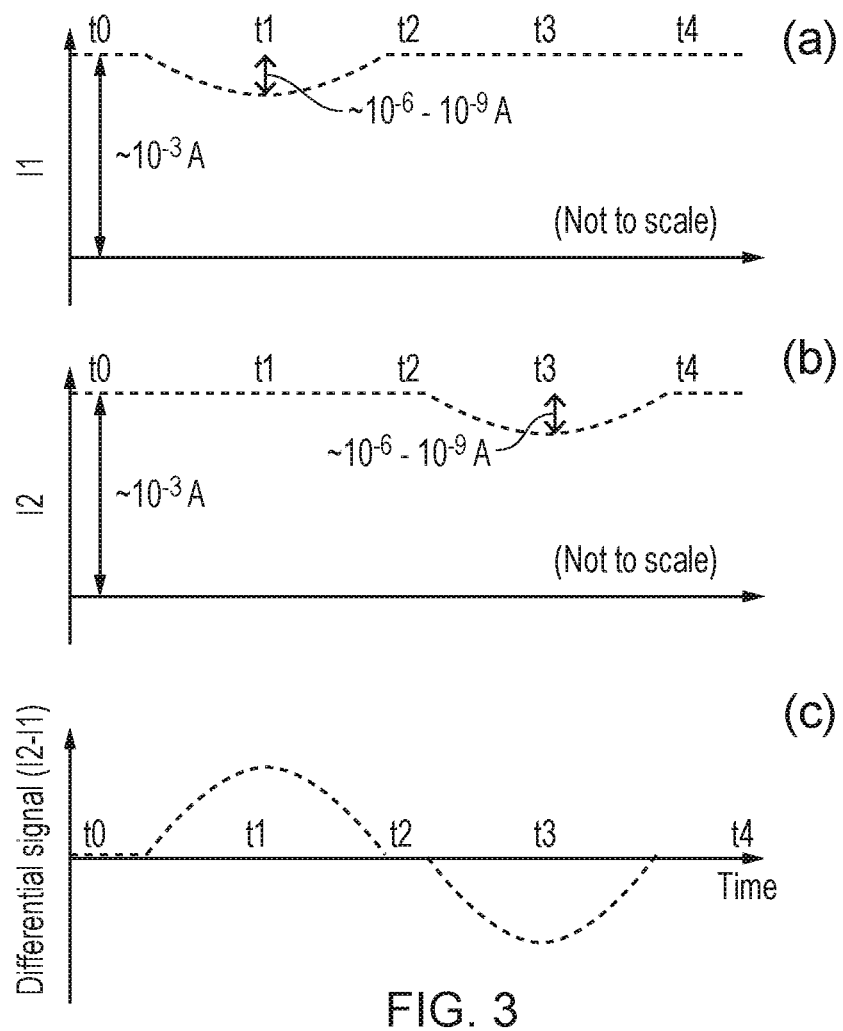
FIGS. 3 (a) to (c) show graphs of current against time and differential current against time measured with the apparatus of FIGS. 1 and 2.

FIG. 2 shows a schematic enlarged view of part of the device of FIG. 1, including the two electrode pairs, arranged across the flow channel 12. A particle 42, which will be a microorganism in an AST procedure, is suspended in fluid flowing along the channel 12. FIG. 3 shows graphs of the detected current over time during an impedance measurement. FIG. 3(a) shows the current I1 detected by the first measurement electrode 32a. FIG. 3(b) shows the current I2 detected by the second measurement electrode 32b. FIG. 3(c) shows the differential signal obtained from the differential amplifier (or other circuitry able to determine a difference signal), representing the difference between the two currents, I2−I1.

At a time t0, the particle 42 is in the channel but yet to encounter the electrodes. Both measurement electrodes 32a, 32b therefore detect substantially the same, non-zero, current since the same voltage (nominally) is supplied to both current paths. Therefore, the differential signal is substantially zero. At a later time t1, the particle 42 passes between the electrodes 30a, 32a of the first electrode pair. It impedes current flow in the first current path, and the detected I1 is reduced, as shown in FIG. 3(a). The second current I2 is largely unaffected by the particle 42. Therefore, the differential signal I2−I1 becomes positive as the particle 42 passes the first electrode pair 30a, 32a, as shown in FIG. 3(c). Then at time t2, the particle is at an intermediate point after the first electrode pair 30a, 32a and before the second electrode pair 30b, 32b, so both currents are again approximately equal and the differential signal returns to zero. At time t3, the particle 42 reaches the second electrode pair 30b, 32b, and impedes the current flow in the second current path. Hence, at t3, the first current I1 has its full value (see FIG. 3(a)), the second current I2 has a reduced value (see FIG. 3(b)), and the differential signal becomes negative (see FIG. 3(c)). At time t4, the particle 42 has flowed out of the measurement region or zone defined by the electrodes, neither current path is affected by the particle 42, and the differential signal is again zero. Appropriate processing of the differential signal can be carried out to deduce the impedance of the particle. The size, structure, shape and composition of the particle determine its impedance properties and hence the effect it has on the current in the current paths defined by the electrode pairs, and on the differential signal. Exposure of a microorganism to an antimicrobial agent to which the microorganism is susceptible will modify the size, structure, shape and/or composition of the microorganism, so that its impedance properties are altered. This is reflected in the differential signal. Accordingly, comparison of the differential signal, or the impedance signal derived from the differential signal, from a sample of microorganisms that has been exposed to an antimicrobial agent to that from a sample of microorganisms that has not been exposed to the antimicrobial agent can indicate whether the microorganisms have any susceptibility to that agent. Hence, AST can be achieved using impedance flow cytometry. Certain cell properties that are modified by antimicrobial treatment show a frequency-dependent response, so utilisation of a voltage with appropriate single or multiple frequency components and processing of the differential signal to extract the impedance response at different frequencies can reveal additional information about susceptibility. Impedance flow cytometry offers advantages over other techniques for AST. For example, it is much faster than disc diffusion and broth microdilution AST and does not require a priori knowledge of the microorganism. Further, the method does not require the addition of costly dyes that are frequently used for optical cytometry, nor are any washing steps needed after exposing the microorganisms to antimicrobials, so impedance flow cytometry can be cheaper and faster than other techniques for AST. It can also be performed in the presence of the antimicrobial agent so that time-dependent changes can be determined.

The currents in the two current paths are typically in the range of 1 to 10 mA, depending on the conductivity of the suspending electrolyte, the dimensions of the channel and the electrodes, and the applied voltage signal. However, the change in the current produced by a passing particle of the size of a microorganism or bacteria cell (which is smaller than a mammalian cell) is in the range of about 1 μA to 1 nA, i.e. between about a thousand to a million times smaller (note that the current plots in FIGS. 3(a) to (c) are not to scale). The differential signal therefore has a small magnitude and is relatively susceptible to noise. In order to maximise the signal-to-noise ratio of the differential signal, the voltage applied to the voltage electrodes can be as high as possible and the gain in the current-to-voltage converters can be maximised. However, as the applied voltage is increased, each of I1 and I2 are increased proportionally, and this leads to clipping in the current to voltage converters and the differential amplifier. Overall, the non-zero currents limit the maximum voltage and gain which can be used, which in turn limits the sensitivity of the device. Another approach for measuring microorganisms with impedance flow cytometry is to reduce the channel size so as to shorten the current paths between the electrodes, so that the small-sized microorganisms have a proportionally greater impact on the detected current (since the size of the microorganisms relative to the channel size is greater). However, narrower channels are prone to blockages, and also increase the backpressure in the channel since this scales with the fourth power of channel size.

Accordingly, an impedance flow cytometer such as the FIG. 1 example has some limitations when measuring particles of a small size, such as microorganisms and bacterial samples for the purpose of AST. Nevertheless, useful AST data can be obtained. The microfluidic flow past electrodes allows detection and measurement of individual microorganisms, so that microorganism counting can be achieved, and data for individual particles within a population of microorganisms in a sample can be obtained and analysed for the total population. Various measurement techniques for AST are described in more detail below with respect to other example impedance flow cytometers; these can also be carried out with apparatus such as that in FIG. 1, or other impedance flow cytometry apparatus.

The present disclosure describes examples of an alternative design for an impedance flow cytometer that can offer improved sensitivity and performance. It can be used in methods to accurately measure samples comprising small particles such as bacteria and/or cells, (or indeed any biological or non-biological particles) in large diameter channels (although smaller channel sizes are not excluded). The device comprises electrodes disposed to create current paths through a microfluidic channel, where the electrodes are configured and driven to provide an improved measurement sensitivity. Hence, impedance flow cytometry can be used for AST and other measurements, tests and assays on bacterial particles, and other biological and non-biological particles. The apparatus has much wider application, however, and can be used to obtain impedance information about any type of particle that can be suspended in an electrolyte fluid for flow in a channel past appropriately configured electrodes.

Figure 4:
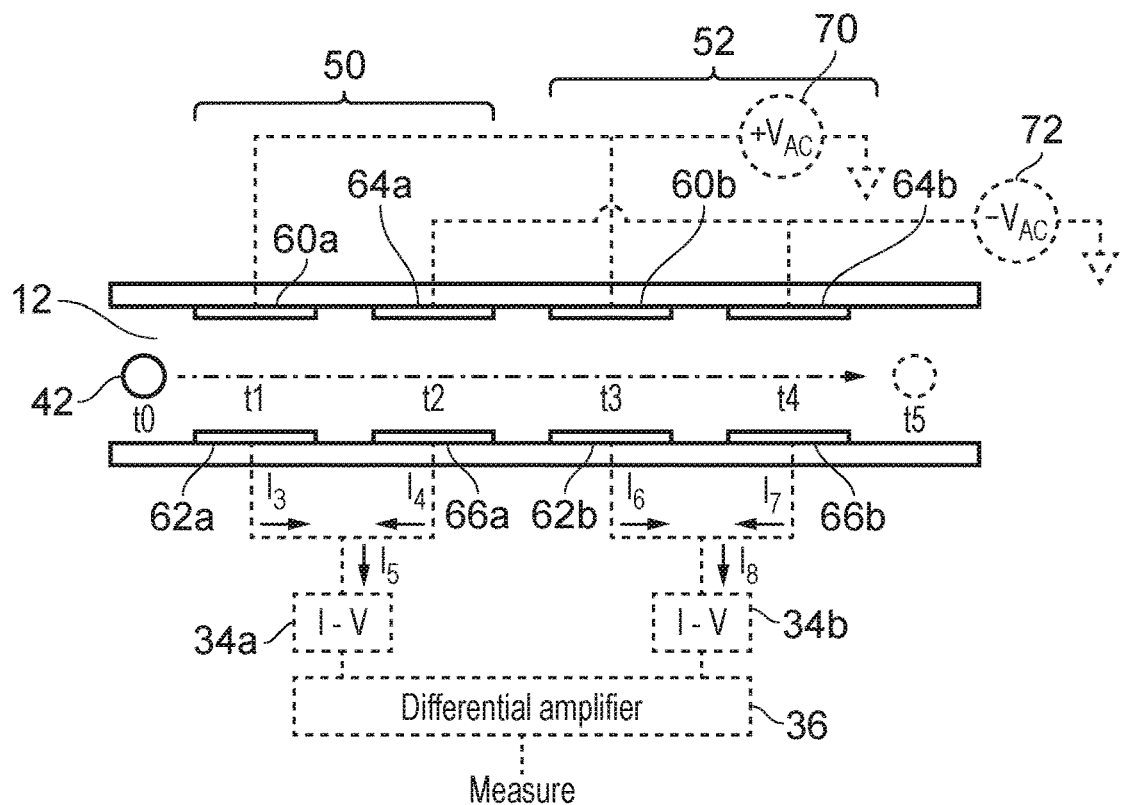
FIG. 4 shows a schematic cross-sectional side view of an electrode and circuitry configuration for an impedance flow cytometer according to a first example of an alternative electrode arrangement.

FIG. 4 shows a schematic cross-sectional side view of a flow channel with electrodes according to an example arrangement. The channel and electrodes may be embodied in a microfluidic chip structure such as that shown in FIG. 1, although other structures and configurations may be used instead. The channel 12 has, in this example, a total of eight associated electrodes. Each electrode is on an inner surface of a flow channel 12 so that is in contact with sample fluid flowing in the flow channel 12. Alternatively the electrodes could be thinly separated from the electrolytic sample fluid.

The electrodes are configured as a first electrode group 50 and a second electrode group 52. The electrodes are configured as either signal electrodes for applying an electrical signal (current or voltage) or measurement electrodes, arranged in pairs to provide current paths through fluid flowing in the channel 12. Each of the first electrode group 50 and the second electrode group 52 provides a first current path from a signal electrode to a measurement electrode, and a second current path from a different signal electrode to a measurement electrode. In the present example, each of these electrodes is separate element. Hence, each electrode group comprises four electrodes, and the device comprises a total of eight electrodes. The first electrode group 50 comprises a first signal electrode 60a above the channel 12 that makes a first current path I3 with a first measurement electrode 62a below the channel 12, and a second signal electrode 64a above the channel 12 that makes a second current path I4 with a second measurement electrode 66a below the channel 12. The second electrode group 52 comprises a further first signal electrode 60b above the channel 12 that makes a further first current path I6 with a further first measurement electrode 62b below the channel 12, and a further second signal electrode 64b above the channel 12 that makes a further second current path I7 with a further second measurement electrode 66b below the channel 12. In this example, the electrodes are arranged in pairs along the flow channel length, so that the further second current path is downstream of the further first current path which is downstream of the second current path which is downstream of the first current path.

Within the first electrode group 50, the first signal electrode 60a is driven with a first voltage +V, which has a specified magnitude, phase and frequency composition (one or more frequencies). In contrast, the second signal electrode 64a is driven with a second voltage −V which has the same magnitude and frequency composition as the first voltage +V, but which is 180° (π radians) out of phase with the first voltage.

The signal electrodes of the second electrode group 52 are driven with the same voltages as the corresponding signal electrodes of the first electrode group 50. Hence, the further first signal electrode 60b is driven with +V and the further second signal electrode is driven with −V, where the magnitudes and frequencies are identical with the first and second voltages of the first electrode group 50. In the FIG. 4 example, this is achieved by supplying the first signal electrode 60a and the further first signal electrode 60b from a first voltage source 70 producing +V, and supplying the second signal electrode 64a and the further second signal electrode 64b from a separate second voltage source 72 producing −V.

Note that it is not essential that the magnitude and frequencies are absolutely identical, and in real-world conditions it is likely that some small differences will occur. Hence, terms such as "same" and "identical" in this context are not limiting, and are intended to include arrangements in which the voltage characteristics are similar or approximately, substantially or nominally the same, for example within boundaries which the skilled person will understand as being acceptable for achieving a meaningful output signal as described herein.

Similarly, a phase difference of precisely 180° is not essential, and the phases may differ by other amounts in the region of 180°. Accordingly, the phases of the two voltages may be considered to be "opposite", where this is intended to include arrangements in which the phase difference is close to or approximately, substantially or nominally 180° (π radians), within boundaries which the skilled person will understand as being acceptable for achieving a meaningful output signal as described herein.

In this example, the signal electrodes are driven at specified voltages from voltage sources, so might be considered to be voltage electrodes. In other examples, the signal electrodes may be driven at specified currents from current sources. Accordingly, the term "signal electrode" is intended to include both alternatives, such that these electrodes provide electrical signals with a frequency, magnitude and phase difference as described and which may be a voltage signal or a current signal. In any of the various examples, voltage sources and voltage electrodes may be substituted with current sources and current electrodes, or vice versa. Similarly, the application of a voltage may more generally be understood as the application of an "electrical signal", which may be a voltage or a current depending on the choice of electrical source.

The measurement electrodes are configured with circuitry that produces a differential signal indicating the difference between measurements from the first electrode group 50 and the second electrode group 52. As shown in FIG. 4, this is implemented in the present example by summing or combining the current I3 detected in the first current path (by the first measurement electrode 62a) with the current I4 detected in the second current path (by the second measurement electrode 66a), to produce a summed signal I5. This first summed signal I5, from the first electrode group, is passed to a current-to-voltage converter 34a. Similarly, the current I6 detected in the further first current path (by the further first measurement electrode 62b) is summed or combined with the current I7 detected in the further second current path (by the further second measurement electrode 66b) to produce a summed signal I8. This second summed signal I8, from the second electrode group, is passed to another current-to-voltage converter 34b. Note that in an alternative arrangement, the circuitry could be configured to implement the current-to-voltage conversions before the summing or combining. In either case, the first summed signal I5, representing the sum of current flow in the first and second current paths of the first electrode group 50, and the second summed signal I8, representing the sum of current flow in the first and second current paths of the second electrode group 52, are passed to further circuitry configured to determine a differential signal that represents the difference between the first summed signal and the second summed signal. In the FIG. 4 example, this comprises a differential amplifier 36. Then, the differential signal can be processed using appropriate processing circuitry or electronics, to calculate from the differential signal an impedance signal indicating the impedance properties or characteristics of the sample fluid, which necessarily includes the impedance properties or characteristics of any particles in the sample fluid. From this, effects of an antimicrobial agent on microorganisms in the sample fluid can be identified by comparison with measurements of impedance from samples of the same microorganisms not treated with antimicrobial agents, or treated with different types or amounts of antimicrobial agent. For example, the differential signal may be inputted to a processor configured to process the differential signal for the purpose of determining impedance signals, impedance values, impedance properties and characteristics of fluid and/or cells, and/or cell counts, as described herein and further below. The circuitry and processing can be implemented with any suitable configuration or combination of hardware, firmware and software, including simple electrical connections, logic gates, amplifiers and central processing units. A single processor or similar processing electronics or circuitry can be used to handle multiple differential signals, for example obtained from multiple flow channels with associated electrodes that may be implemented on a single substrate or chip. An apparatus configured in this way enables simultaneous measurements to be obtained simply for multiple samples. In the context of microorganism testing, this can allow a reference sample of untreated microorganisms to be measured at the same time as a treated sample, or multiple samples of a particular microorganism to be tested with different antimicrobial agents, or multiple samples of a particular microorganism to be tested with different concentrations of the same antimicrobial agent to determine the so-called minimum inhibitory concentration. Derivation of the differential signal can be understood from FIG. 5, which shows graphs of current against time for the two summed signals (a) and (b), and the corresponding differential signal (c).

Figure 5:
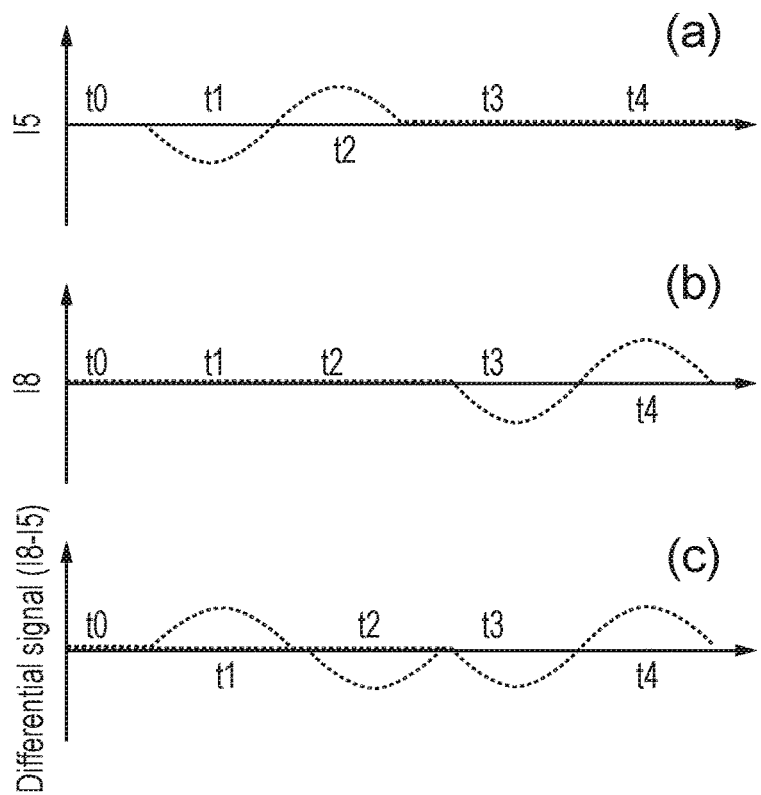
FIG. 5 (a) to (c) shows graphs of summed current against time and differential summed current against time measured by a method using the apparatus of FIG. 4.

FIG. 4 shows a particle 42, such as a bacterial cell, in the flow channel 12 at a position in which it is upstream of the first electrode group 50, and about to enter a measurement region defined by the electrodes. By time t5, the particle 42 has passed all the electrodes and exited the measurement region. The graphs in FIG. 5 show the various signals at t0 and subsequent times t1 to t4 before t5. For convenience and simplicity, the fluid sample may have a cell concentration and a flow speed along the fluid channel that is intended to provide only one particle at a time in the measurement region, being the zone within which the electric fields of the electrodes are present.

At t0, the particle 42 is outside the measurement region, and does not interact with any of the current paths. Hence, in the first electrode group 50, the first measurement electrode 62a detects a current I3 in the first current path which is the same magnitude but opposite phase to the current I4 in the second current path detected by the second measurement electrode 66a. Therefore, I3 and I4 cancel one another out, and their sum is zero (or approximately zero, given any minor differences in the electrical signals delivered by the signal electrodes), giving a first summed signal I5 of zero at t0, as in FIG. 5(a). Similarly, in the second electrode group 52 the current I6 at the further first measurement electrode 62b is equal but opposite to the current I7 at the further second measurement electrode 66b, so that their sum is also approximately zero, giving a second summed signal I8 of zero, shown in FIG. 5(b). Therefore, at t0, the differential signal I8−I5 is also zero, as shown in FIG. 5(c). Hence, the "background" signal measured by the apparatus, when no particle is present, is substantially zero-valued and obtained from the difference of two zero-valued measurements. Accordingly, the voltages applied at the voltage electrodes can be raised to a high value without the detected signals undergoing any clipping in the converters 34 or the differential amplifier 36, so the measurement sensitivity can be maximised within the capability of the voltage sources.

At time t1, the particle is between the first signal electrode 60a and the first measurement electrode 62a, so impedes the current flow in the first current path. I3 is therefore reduced. The current flow I4 in the second current path, between the second signal electrode 64a and the second measurement electrode 66a, remains as before. The first summed signal I5, being I3+I4, is therefore also reduced. The second summed signal I8, being I6+I7 from the second electrode group, remains at approximately zero, since no particle is in either of these current paths. The differential signal I8−I5 therefore becomes positive, owing to the reduced value of I5. At t2, the particle 42 has moved to be between the second signal electrode 64a and the second measurement electrode 66a. The current I3 in the first current path resumes its previous value, and the current I4 in the second current path is reduced, by the presence of the particle 42. Recall that the second signal electrode has a negative driving voltage, however, so that the first summed signal I5=I3+I4 becomes positive, as shown in FIG. 5(a). The second summed signal I8 remains at approximately zero. Accordingly, the differential signal I8−I5 becomes negative at t2.

At time t3 and then later at time t4, the particle enters the second electrode group 52, and interacts with the further first current path I6 at t3, and then the further second current path I7 at t4. Since the further first current path I6 has the same voltage supply as the first current path I2, and the further second current path I7 has the same voltage supply as the second current path I4, the second summed signal follows the same shape at times t3 and t4 as the first summed signal showed at times t1 and t2, becoming negative in t3 and positive in t4. Meanwhile, the first summed signal I5 remains zero during these times since no particle is present in the part of the measurement region corresponding to the first electrode group. Hence, in t3, the differential signal I8−I5 goes negative, and then becomes positive in t4, as shown in FIG. 5(c).

At t5, the particle has left the measurement region, so all four current paths are unperturbed. Both summed signals will be substantially zero, giving a zero-valued differential signal, as at time t0.

Note the particular shape of the curve followed by the differential signal, shown in FIG. 5(c). The sequential arrangement along the channel length of the two electrode groups 50, 52 and the four pairs of electrodes with the groups, together with the alternating arrangement of positive and negative voltages for the signal electrodes along the channel length, gives a corresponding differential signal that shows positive then negative then negative than positive features over time, as a particle passes along the measurement region. This shape is more distinct compared to noise than the differential signal from the FIG. 1 apparatus, so can be more readily distinguished (using signal processing techniques). This enhances the signal to noise ratio, further improving the sensitivity.

The differential signal may alternatively be calculated as I5-I8, if preferred, i.e. the first summed signal minus the second summed signal. In either case, the differential signal represents the difference between the summed signals, and the impedance properties of the particle can be determined from it. This is also applicable to examples described further below.

This electrode configuration (and similar configurations enabling the same result) and its improved performance enables meaningful impedance measurements to be obtained for small particles such as bacteria flowing in a large channel. This reduces the risk of blockages of the channel, and makes such an apparatus more usable in real-world environments and situations. Bacterial cells typically range in size from 0.2 to 2 μm. By "a large channel", it is meant that the dimensions of the channel in the plane transverse to the fluid flow direction are in the range of about 10 to 50 μm, such as 20 μm. As an example, the channel may have a square cross-section (arising for example from the layered construction and formation with photolithography) with a substantially equal width and height of about 40 μm. Alternatively, the channel may have a height, being a dimension orthogonal to a plane of the substrate on which the apparatus is formed and to the direction of flow, and parallel to the current flow path from a voltage electrode to a measurement electrode, of about 10 to 50 μm, such as about 20 μm, with the transverse (width) dimension, being larger. Other dimensions may also be used, such as a channel with a smaller dimension in the range of 100 to 1000 μm suitable for measuring cells about 10 μm across, or still larger channels able to accommodate particles on the millimetre scale.

Other electrode configurations may be used to obtain the same or similar signals from which impedance characteristics of particles in the sample fluid may be deduced. A variety of arrangements comprising a first electrode group and a second electrode group each providing a first current path and a second current path driven at approximately equal but approximately opposite voltages is possible. Within a group, the first current path and the second current path may be at different locations along the flow direction of the channel, as in FIG. 4. The first electrode group and the second electrode group may also be at different locations along the flow direction of the channel, also as in FIG. 4. The electrodes of each group need not be physically grouped together, however, and may be dispersed among electrodes of the other group.

Figure 6:
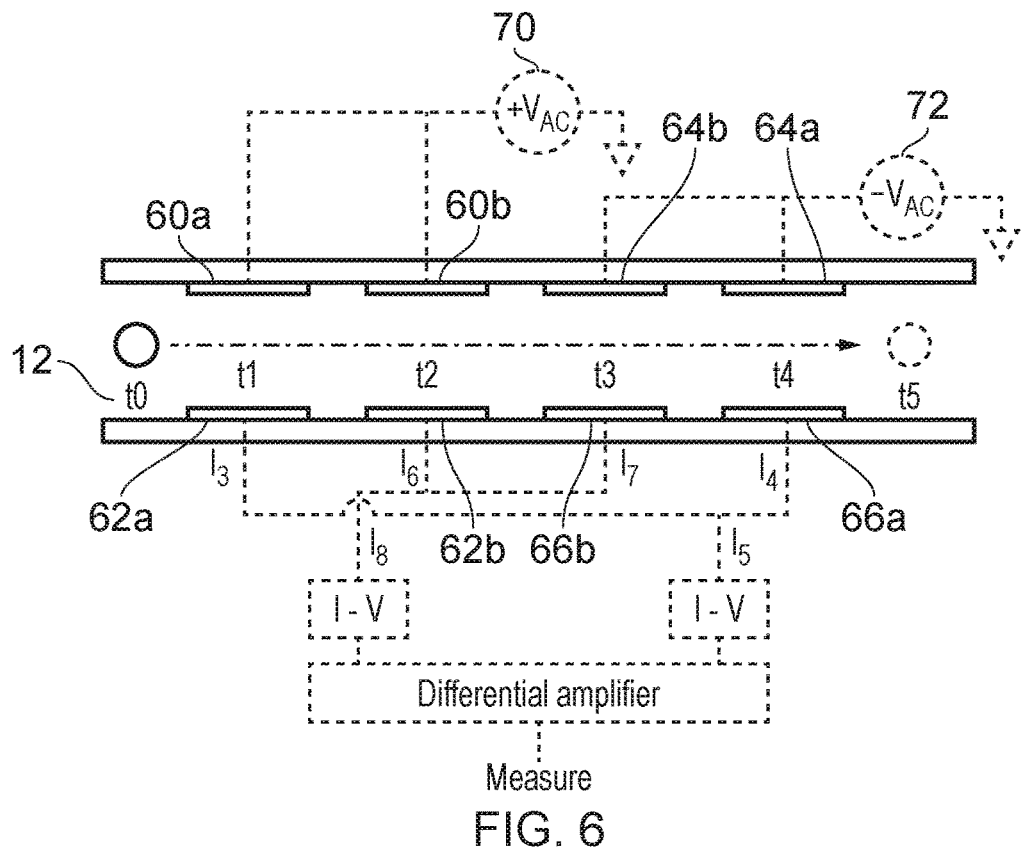
FIG. 6 shows a schematic cross-sectional side view of an electrode and circuitry configuration for an impedance flow cytometer according to a second example.

FIG. 6 shows a second example, in a schematic cross-sectional side view including the same elements as FIG. 4. Hence, eight electrodes are included, comprising four signal electrodes and four measurement electrodes disposed as four pairs across the flow channel 12. However, in this example, the signal electrodes of each electrode group are alternated along the flow channel. Thus, in order along the flow channel 12, the measurement region comprises firstly the first signal electrode 60a and its first measurement electrode 62a to give the first current path I3, secondly the further first signal electrode 60b and its further first measurement electrode 62b to give the further first current path I6, thirdly the further second signal electrode 64b and its further second measurement electrode 66b to give the further second current path I7, and lastly the second signal electrode 64a and its second measurement electrode 66a to give the second current path I4. The first current path I3 and the second current path I4 are combined for the first summed signal I5, and the further first current path I6 and the further second current path I7 are combined for the second summed signal I8, as before. The time evolution of the differential signal for a particle traversing the measurement region will be differently shaped from that shown in FIG. 5(c)—it will comprise positive then negative then positive than negative features— but can be distinguished from noise by appropriate filtering and/or signal processing.

The examples of FIGS. 4 and 6 both comprise separate voltage sources (or current sources) to supply the first electrical signal to the first signal electrodes in each group and the opposite second electrical signal to the second signal electrodes in each group. The signal electrodes are connected to one side of the voltage source, and the other side is connected to ground.

Figure 7:
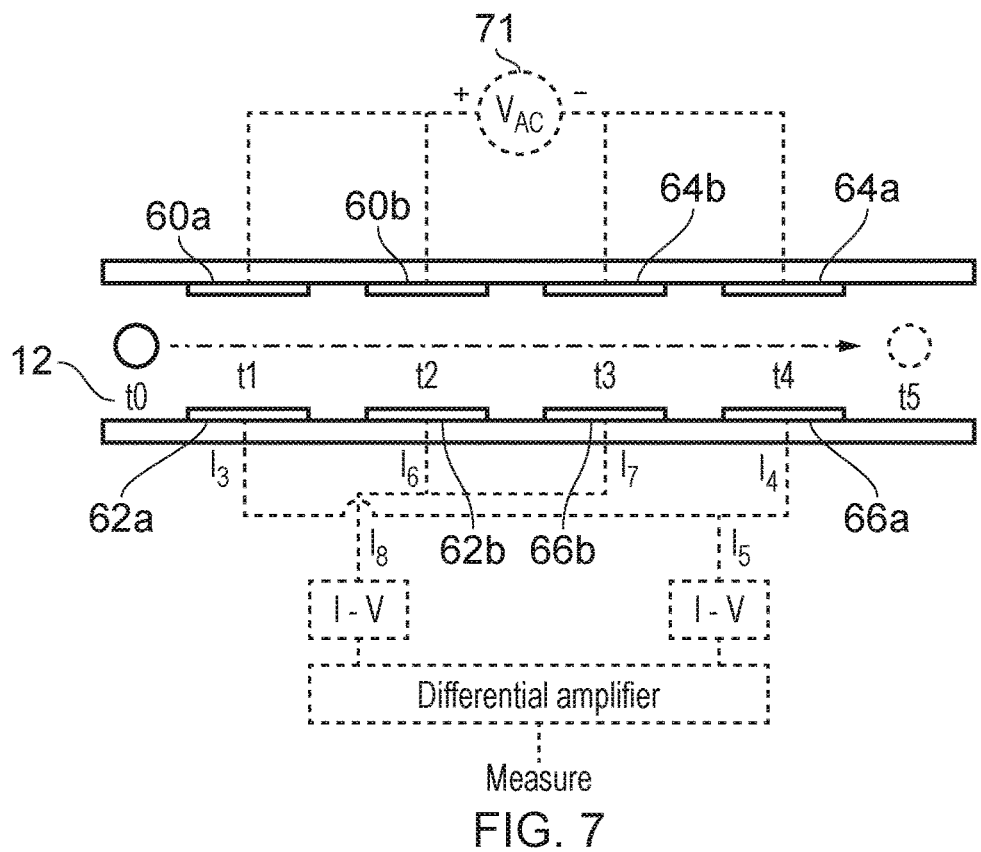
FIG. 7 shows a schematic cross-sectional side view of an electrode and circuitry configuration for an impedance flow cytometer according to a third example.

FIG. 7 shows a schematic cross-sectional side view of an alternative example that is simplified by use of a single voltage source to drive all the signal electrodes. This example comprises eight electrodes, positioned the same as in the FIG. 6 example. A single voltage source 71 drives all the signal electrodes. The first signal electrodes 60a, 60b of each electrode group are connected to the positive side of the voltage source 71 to receive +V, and the second signal electrodes 64a, 64b of each electrode group are connected to the negative side of the voltage source 71 to receive –V.

Figure 8:
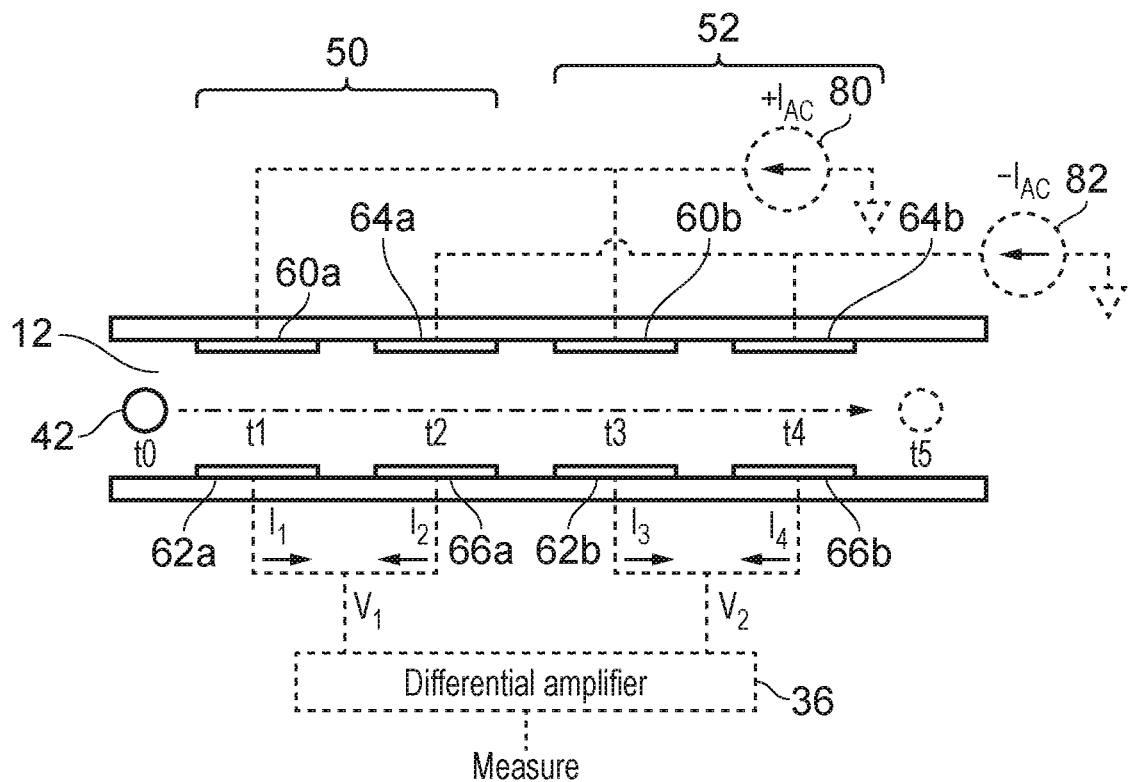
FIG. 8 shows a schematic cross-sectional side view of an electrode and circuitry configuration for an impedance flow cytometer according to another example.

As has been noted, the apparatus may be driven using voltages or currents applied to the signal electrodes. FIG. 8 shows an example apparatus configured as the FIG. 4 example, but using current sources in place of voltage sources. Components are otherwise the same so are not described in detail here. A first current source 80 provides a current with a magnitude, phase and frequency composition to the first signal electrodes 60a, 60b of each of the first and second electrode groups 50, 52. A second current source 82 provides a current with substantially the same magnitude and phase to the second signal electrodes 64a, 64b of each electrode group 50, 52, but which is negative compared to the current from the first current source 80 in that it has an opposite or approximately opposite phase (the phase difference between the two currents is about 180° or π radians). Voltages V1 and V2 representing the summed signals from the measurement electrodes 62a, 66a, 62b, 66b of each electrode group 50, 52 are input to a differential amplifier 36 to allow the differential signal to be determined.

Other configurations for the electrodes and the resultant current paths are also possible. Typically the electrodes will be above and below the flow channel owing to the constraints of conventional fabrication of a layered microfluidic structure, but this is not essential for operation, and the apparatus may be configured with electrodes disposed about the channel in other orientations. In an example, the positive and negative signal electrodes may be placed adjacently as in the FIG. 6 example, but with measurement electrodes of the first group placed as the two central measurement electrodes and measurement electrodes of the second group placed as the two outer measurement electrodes, opposite to the FIG. 6 arrangement. The examples so far have all comprised signal electrodes at the top of the flow channel and measurement electrodes at the bottom of the channel. This is not a limitation, however, and any of the electrodes may be placed in either position, perhaps according to convenience in connecting them with the voltage or current source(s) (electrical signal sources) and the measurement circuitry. For example, the electrodes of one or more pairs of signal electrode and measurement electrode may be oppositely arranged so that the measurement electrode is above the channel and the signal electrode is below the channel. Further, the individual electrodes may be combined in larger electrodes that perform the function of two individual electrodes, for example where those electrodes are physically adjacent. Considering the FIG. 4 example, the first measurement electrode and the second measurement electrode, in the first electrode group, are adjacent, and the further first measurement electrode and the further second measurement electrode, in the second electrode group, are adjacent, and downstream from the first and second measurement electrodes. This allows the first and second measurement electrodes to be replaced with a single combined electrode that collects the current from both the first current path and the second current path, so that its output is already a combined or summed signal from the first electrode group. Similarly, the further first measurement electrode and the further second measurement electrode can be replaced by a single combined electrode that outputs the summed signal representing the first and second current paths of the second electrode group. Signal electrodes may also be combined into a single larger electrode. Within an electrode group as described thus far, the signal electrodes comprise two electrodes that apply different, opposite electrical signals (voltage or current) to the two current paths of that group. Therefore, the signal electrodes within a group cannot be combined. However, the same voltages or currents (nominally) are applied to corresponding positive and negative signal electrodes in the two different electrode groups, giving scope for signal electrodes to be combined or shared across the electrode groups. Thus far, the examples have comprised electrodes paired to provide current paths that pass through the fluid channel in a direction roughly transverse to the fluid flow direction; this is achieved by the paired electrodes being disposed on opposite sides of the channel. This is not essential however, and the current paths may be otherwise situated, in any arrangement that allows suspended particles to interact with the electric fields emanating from the voltage electrodes and hence modify the current flow in the current paths. For example, the electrodes can be arranged so that signal electrodes and measurement electrodes alternate along the upper and lower sides of the channel, but are arranged opposite to a same type of electrode. Hence, the signal electrodes producing the same electrical signal are opposite to one another, and the electric fields are directed along the direction of the channel length to the adjacent measurement electrodes. Such an arrangement provides current paths which are substantially along, or parallel to, the fluid flow direction through the channel. The electrodes may be planar, which is convenient in a chip-based device fabricated in layers, but this is not essential. For example, the electrodes may be formed as rings or collars sequentially surrounding the channel, which might be of circular or oval cross-section, formed from a pipe or tube, for example.

In further examples, the number of electrodes may be increased, to provide additional current paths. This will increase the distinctive nature of the pattern of the differential signal, making it easier to isolate from noise and hence improving the sensitivity. The number of electrode groups is maintained as two, and within each group, extra electrodes provide additional first and second current paths. The particle impedance signal can be extracted from height-related features of peaks and troughs in the summed signal and/or the differential signal. This can be accomplished by measuring the amplitude of the peaks and/or troughs, or matching the shape of the signal to templates obtained for particles with known characteristics, for example. The sequence of the peaks and troughs in the summed signals and/or the final differential signal can be designed by choosing the relative sequence of the signal electrodes. It is known from signal processing mathematics that some signal shapes are more unique than others, so that an improved signal to noise ratio can be obtained by an appropriate sequence of the electrodes along the flow channel.

As discussed, the various described examples of impedance flow cytometry apparatus are applicable to measurements of bacteria and microorganism samples, such as AST, where the examples of FIGS. 4 to 8 are particularly beneficial for this purpose compared to the example of FIGS. 1 to 3 because they can process small sized particles with measurement sensitivity sufficient to obtain meaningful data. Thus, the presently disclosed impedance flow cytometers and their use have application for improved diagnosis of microbial infection and prescription of antimicrobial agents. Furthermore, in the examples of FIGS. 4 to 8 the flow channel of the apparatus is able to have significantly larger dimensions than typical bacterial cell sizes, so apparatus of this type is also useful for measurements of samples of non-bacterial cells, which typically have a larger size than bacterial cells, or for mixed samples containing a range of particle sizes, and indeed for particles of non-biological origin.

Various example measurement techniques and procedures that can be implemented using impedance flow cytometry will now be described. The descriptions are made with reference to apparatus such as the FIGS. 4 to 8 examples, but in general, these and similar methods may also be implemented using an apparatus such as the FIGS. 1 to 3 example.

The differential signal generated by the impedance flow cytometry apparatus has a particular shape (the exact details of which depend on the ordering of the various electrodes, which can be selected to increase the distinctiveness of the signal shape or pattern), so at a simple level, the apparatus may be used for particle or cell counting. The processing of the differential signal may comprise a simple identification and count of all occurrences of the particular shape of the signal that arises from the passage of a particle through the measurement region. This can be used for counting of regular cells, but is also applicable to identification of biological susceptibility to antimicrobial agents.

Some antimicrobial agents act by disrupting the structural integrity of the microorganisms, so that if a strain of microorganism is susceptible to an antimicrobial agent of this type, exposure of the sample to the antimicrobial agent will over time reduce the population of microorganisms in the sample. This can be identified by counting the number of treated microorganisms in an accurately volume-measured sample and comparing it to the count of a sample of untreated microorganisms at a specified time point or series of time points. Simple analysis of this type may not require any detailed calculation or analysis of the actual values of impedance of particles in the fluid sample; there may not be a need to derive an impedance signal from the differential signal, or to identify impedance values, properties or characteristics of the particles from the impedance signal.

However, analysis of the impedance signal can reveal additional valuable information about cells, and microbial susceptibility to antimicrobial agents in particular. Methods according to the present disclosure enable a range of impedance-based measurements to be made that can reveal information about biological and non-biological particles, including cells and bacteria, in a simple and rapid manner with a minimal number of steps.

Different classes of antimicrobial agents have different modes of operation, and produce different biophysical changes in microorganisms. As noted above, some antimicrobial agents disrupt the structural integrity of microorganisms, thereby reducing the population size, which can be detected via a particle count in an accurate sample volume. Other antimicrobial agents operate by inhibiting cell wall synthesis, which can produce an overall increase in cell volume (size). The cell wall or cell membrane properties themselves may be altered, such as a change in thickness, electrical or material properties, or porosity, and the internal cell structure or composition may change. These various characteristics—cell size, cell wall/membrane properties, internal properties—all contribute to the impedance properties or value of the cell. Accordingly, measurement of the impedance of particles in a sample can reveal characteristics of the cells. Comparison between measurements of samples of microorganisms treated and untreated with antimicrobial agents to identify any differences can reveal if the characteristics have been changed by the antimicrobial exposure, indicating a measurable susceptibility to the antimicrobial agent. The antimicrobial agent can remain in the sample for the cytometry measurement, or may be removed by washing before the measurement if preferred. There is no need for removal, however, which is a beneficial aspect of the method herein compared to optical cytometry techniques, in which it is typically necessary to remove an antimicrobial agent from a sample before adding a necessary dye. To determine susceptibility, a threshold level for a change in one or more characteristics reflected in the impedance measurement can be set. If comparison between impedance signals from antimicrobial agent unexposed and exposed microorganism samples shows that the amount of change is at or above the threshold, susceptibility can be recognised. The threshold might be, for example, a threshold for a change in the measured size of a characteristic, or a threshold for the number of microorganisms in the sample exhibiting that change, for example.

On a simple level, the magnitude of the differential signal obtained using an apparatus as described herein, an example of which is shown in FIG. 5(c), has a dependence on particle size. A larger particle has a greater effect on or interaction with the electric field in the flow channel, so the current flow is reduced more, and a lower current is detected at the measurement electrode. The differential signal will therefore contain peaks and troughs of a larger amplitude than for a smaller particle. Comparison of a measurement from exposed microorganisms with that from unexposed microorganisms may therefore reveal antimicrobial susceptibility if the differential signal from the former measurement shows larger amplitude features than the latter sample. One may consider the differential signal directly for this analysis, or calculate corresponding impedance values from the differential signal.

When considering impedance values, recall that impedance comprises two parts or components, the real part and the imaginary part, or more usefully, the magnitude |Z| and the phase θ. Any value or combination of these components may be analysed to investigate properties of particles in a sample fluid. Moreover, the nature of the interaction of a particle with the electric field depends on the frequency of the electric field. Hence, different impedance results can be obtained by measuring at different frequencies or more than one frequency, and these can reveal different characteristics of the particle. The measurement might be done by studying one sample of microorganism at one frequency and studying another sample of the same microorganism at a second frequency, by connecting a different voltage or current source to the signal electrodes or setting the signal source to output a different frequency to the signal electrodes. More conveniently, however, the signal source or sources used to drive the signal electrodes can be configured to output more than one frequency at the same time. Appropriate filtering and/or processing of the differential signal or the impedance signal derived from it can be carried out to isolate the different frequency components in the recorded measurements, so that one or more impedance components (e.g. magnitude and/or phase) can be obtained for each frequency component.

Figure 9:
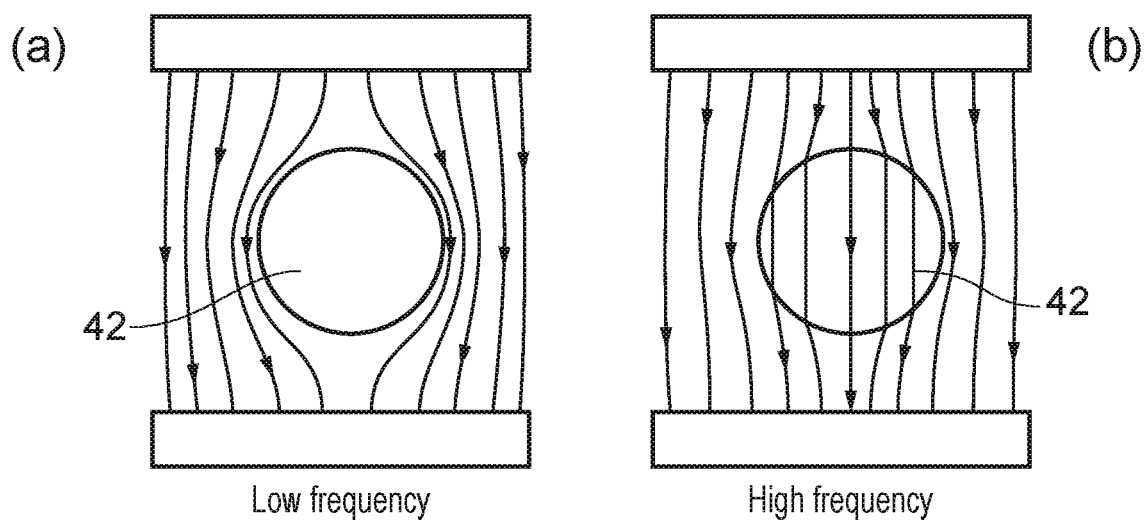
FIG. 9 (a) and (b) show schematic depictions of the interaction of a cell with an electric field at low and high frequencies.

FIG. 9 shows representations of the interaction of a particle (cell) with electric fields of different frequencies. A cell 42 suspended in an electrolytic fluid is in an electric field (indicated by the lines), such as would be present in the flow channel between a signal electrode and a measurement electrode. In FIG. 9(a), the frequency is low, by which is meant a frequency in the range of about 10 MHz or less, such as about 1 MHz or about 5 MHz. In this regime, the electric field passes around the cell 42 (note that the electric field lines do not penetrate into the cell and are diverted around it), and the measured impedance signal reflects the electric volume of the cell (representative of the cell's physical size). Accordingly, the cube root of the measured impedance magnitude, $|Z|^{1/3}$, approximately reflects the electric radius. In FIG. 9(b), the frequency is high, by which is meant a frequency greater than the low frequency, for example a frequency which is greater than about 10 MHz, such as about 40 MHz. In this regime, the electric field capacitively couples across the wall (membrane) of the cell 42 (note that the electric field lines pass through the cell relatively unperturbed). The effect of this is that the measured impedance signal reflects the electrical properties of the cell wall and/or membrane and/or the cytoplasmic properties of the cell's interior. This can be termed the "electric opacity". Accordingly, differences in these characteristics between two cells will be apparent as differences between the measured impedances at a high frequency. Note that useful values for high and low frequencies will be different, or significantly different, from these example values for other cell types, other particle types, and/or different conductivities of the suspending electrolyte. For example, values for a high frequency of about 1 MHz for non-bacterial cells and about 10 MHz for bacterial cells in a suspending medium with a conductivity similar to physiological media might be suitable. A low frequency is one at which the electric field generally does not penetrate the particle, and from which size information about the particle can be deduced. A high frequency is one which is higher than a chosen low frequency, and at which the electric field couples across the cell wall, allowing properties dependent on the cell's membrane and wall to be investigated. At much higher frequencies (about 5 MHz or above for non-bacterial cells and about 50 MHz or above for bacteria, considered to be within a high frequency regime for the present disclosure), internal structure and component parts can be measured.

Hence, there is a distinction between measurements at different frequencies (particularly between low frequencies and high frequencies as defined above) of the same particle that depend on properties of that particle, from which information about those properties can be deduced. Other parameters also affect the distinction, including the conductivity and permittivity of the suspending electrolyte fluid, but this and other parameters which are features of the apparatus and the testing regime or protocol can be kept constant across multiple measurements so do not impact on comparative analyses.

Measurements may be obtained at a single frequency only, which may be high or low, or at more than one frequency, typically two, either sequentially or simultaneously.

An approach for two frequencies is, for an individual particle, to calculate the impedance (magnitude, phase, real or imaginary components) at the low frequency, and the impedance at the high frequency. These values are plotted on a graph, together with the values for other particles in the same sample, to produce a scatter plot. The low frequency impedance magnitude, indicating the electric radius or electric volume, may be plotted on the x-axis of the graph, and the high frequency impedance magnitude may be plotted on the y-axis of the graph. Alternatively, the y-axis may plot the ratio of the high frequency value to the low frequency value, thereby normalising the opacity to the cell size; this is termed "electrical opacity".

Figure 10:
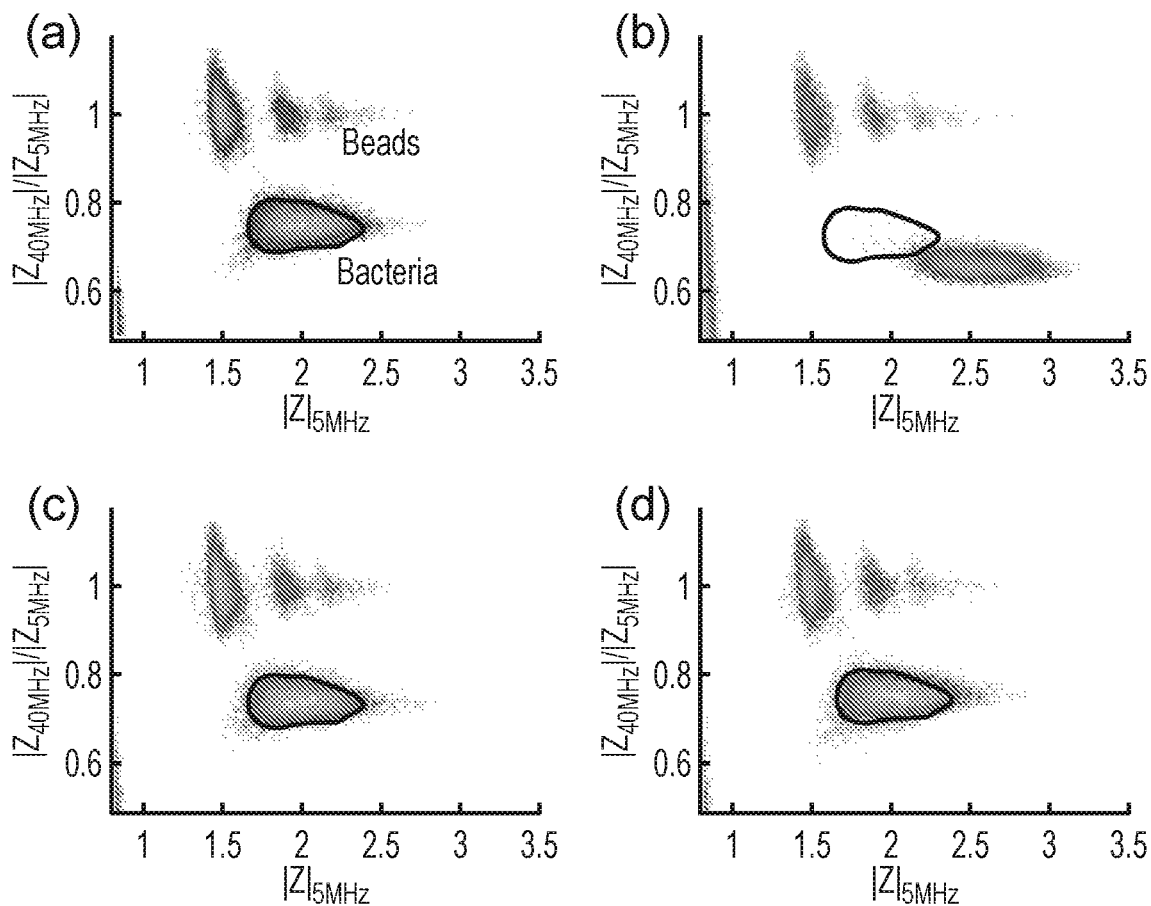
FIGS. 10 (a), (b), (c) and (d) show example scatter plots of impedance data recorded from bacterial cell samples at two frequencies with an impedance flow cytometry method according to an example of the present disclosure, showing an antimicrobial effect on susceptible and resistant bacteria strains.

FIG. 10 shows four example scatter plots. FIG. 10(a) shows measurements for a bacterial strain that has not been treated with any antimicrobial. The measurements were obtained at two frequencies, a low frequency of 5 MHz and a high frequency of 40 MHz. The impedance value for each cell at the low frequency, $|Z|_{5\ MHz}$, is plotted on the x-axis, and the normalised impedance value for each cell at the high frequency, $|Z|_{40\ MHz}/|Z|_{5\ MHz}$, is plotted on the y-axis. Each data point corresponds to an individual particle in the sample. For calibration/reference purposes, the sample included a quantity of plastic micro-beads, of a known size which may be broadly comparable to the bacteria size, and known dielectric properties (known impedance characteristics). The beads appear on the graph centred around a high frequency value of 1, and a low frequency value of 1.5, for single beads. Bead which become stuck together into doublet and triplet groups appear as smaller populations at higher low frequency values, to the right of the main bead population. However, all the beads are well-separated from the data points representing the bacterial cells in the sample. These are centred on a high frequency value of about 0.75, extending over a low frequency range of about 1.6 to 2.4. A closed solid line is superimposed over the bacteria data points to indicate the location of the bulk of the bacterial population. This line can be considered as a contour line or boundary, or a gate, and is useful for comparing measurements from different samples. It can be drawn to encompass all the data points of the bacteria, or a central proportion of the data points such as 99%, 95%, or 90% so that outlying measurements are excluded. Known statistical techniques can be utilised to place and size the contour.

FIG. 10(b) shows measurements for a sample of the same bacterial strain which has been incubated with an antimicrobial agent, in this example, from an antimicrobial class called β-lactams, for 30 minutes. The data points for the beads are unchanged from FIG. 10(a), since the antimicrobial has no effect on the plastic material. The data for the bacteria, however, have shifted significantly to higher impedance values at the low frequency, now occupying a range of about 2.1 to 3, and shifted somewhat to lower impedance values at the high frequency, now centred at about 0.7. The solid contour line from FIG. 10(a) is reproduced in FIG. 10(b). Almost no data points lie within the solid line, indicating that virtually the entire population of bacteria has been substantially modified by the antimicrobial agent. The shift to larger low frequency values indicates an increased electric radius, and the shift to smaller high frequency values indicates a change in the internal cell structure and/or the cell wall. Accordingly, we deduce that the antimicrobial agent has had a measurable effect on the bacteria, so the bacteria are susceptible to that particular antimicrobial agent. β-lactam antimicrobial agents inhibit cell wall synthesis and hence have an overall effect of increasing the volume (size, diameter) of the bacteria, as observed in FIG. 10(b).

FIGS. 10(c) and 10(d) show two more scatter plots for samples of exposed and unexposed bacteria plus plastic beads, where the bacteria are a different strain from that of FIGS. 10(a) and 10(b). FIG. 10(c) shows data for a sample of the bacteria which has not been exposed to an antimicrobial agent. A contour line is drawn around the bacteria population as before. FIG. 10(d) shows data for a sample of the bacteria after exposure to the β-lactam antimicrobial agent. Very little difference from FIG. 10(c) can be observed; almost the whole bacteria population remains inside the contour line. Accordingly, we can deduce that the antimicrobial agent has had little, if any, measurable effect on the bacteria. The strain being tested are concluded to be resistant to the antimicrobial agent at this specific concentration.

As noted above, other classes of antimicrobial have different effects on microorganisms. To determine whether a population of microorganisms is susceptible to a particular antimicrobial agent, any or all of three different parameters can be assessed from the impedance measurement. A change in cell size is indicated by a change in the response at lower frequencies (the x-axis in FIGS. 10(a)-(d)), and a change in cell wall/cell interior properties is indicated by a change in the response at higher frequencies (the y-axis in FIGS. 10(a)-(d)). A reduction in the total particle population arising from compromised cell structure due to the antimicrobial agent to such an extent that it no longer registers as a particle is indicated by a reduced particle count in an accurately measured volume. Each of these changes produces a smaller number of data points inside a contour such as that shown in FIGS. 10(a)-(d), either because the data points migrate outside the contour if the cell size or wall/interior structure changes, or because the data points are eliminated if the cell integrity is compromised. Accordingly, a comparison of the number of data points inside the same contour line for exposed and unexposed microorganism populations can be used to identify susceptibility. A metric representing susceptibility at a specific antimicrobial concentration can be defined as the number or proportion of microorganisms in an exposed sample that lie inside the contour drawn for the unexposed sample. For example, in FIG. 10(b) very few cells are left within the contour, and the metric is close to 0%; therefore the bacteria are susceptible to the antimicrobial agent at that concentration. In FIG. 10(d) most of the cells lie inside the contour, and the metric is close to 100%; therefore the bacteria are resistant to the antimicrobial.

Figure 11:
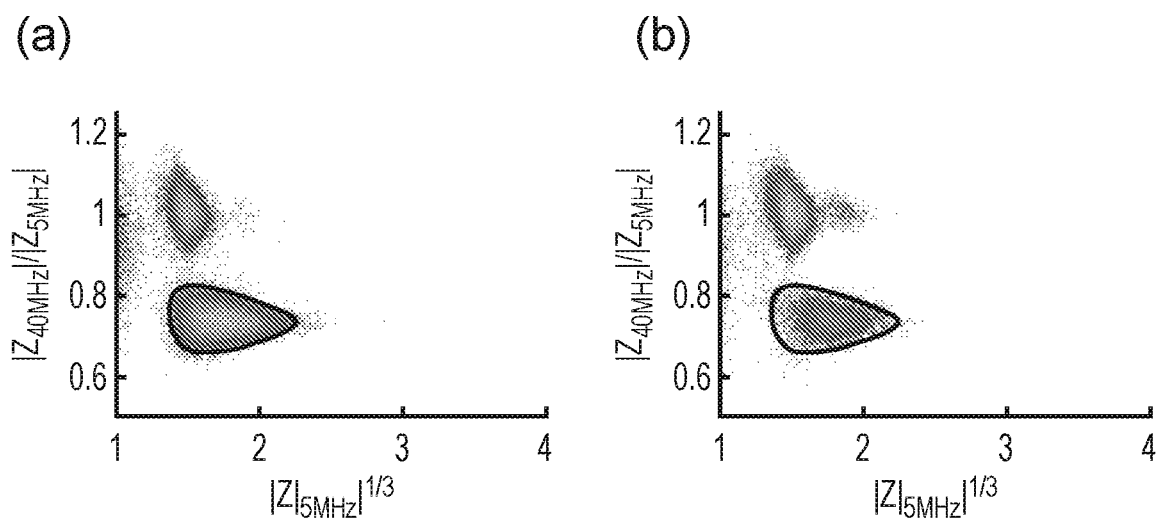
FIGS. 11(a) and (b) show example scatter plots of impedance data recorded from bacterial cell samples at two frequencies with an impedance flow cytometry method according to an example of the disclosure, showing a further effect of antimicrobial agent on susceptible bacteria.

FIGS. 11(a) and (b) show some example scatter plots indicating susceptibility to an antimicrobial agent that reduces the total cell count by destroying the bacteria. For each plot, the electric radius for each cell at the low frequency, $|Z_{5\ MHz}|^{1/3}$, is plotted on the x-axis, and the normalised impedance value for each cell at the high frequency, $|Z|_{40\ MHz}/|Z|_{5\ MHz}$, is plotted on the y-axis, as with the FIG. 10 graphs. FIG. 11(a) shows impedance measurements from an unexposed sample, including a population of bacteria, with a contour line or gate drawn to encompass the bulk of the population, and a population of reference beads at a larger high frequency response. FIG. 11(b) shows impedance measurements from an exposed population. The x-y position of the data has not moved significantly for the exposed bacteria, since there are few data points outside the contour, but the total cell count is substantially reduced, indicated by the smaller number of data points inside the contour compared with the unexposed sample. Therefore, the bacteria are classified as susceptible to the particular antimicrobial agent.

The example data described so far has been obtained using a high frequency and a low frequency for the signal applied to the signal electrodes in the apparatus. However, results may also be obtained by measuring at one frequency only. A scatter plot for a microorganism population may then be produced by plotting the impedance magnitude against the impedance phase.

Figure 12:
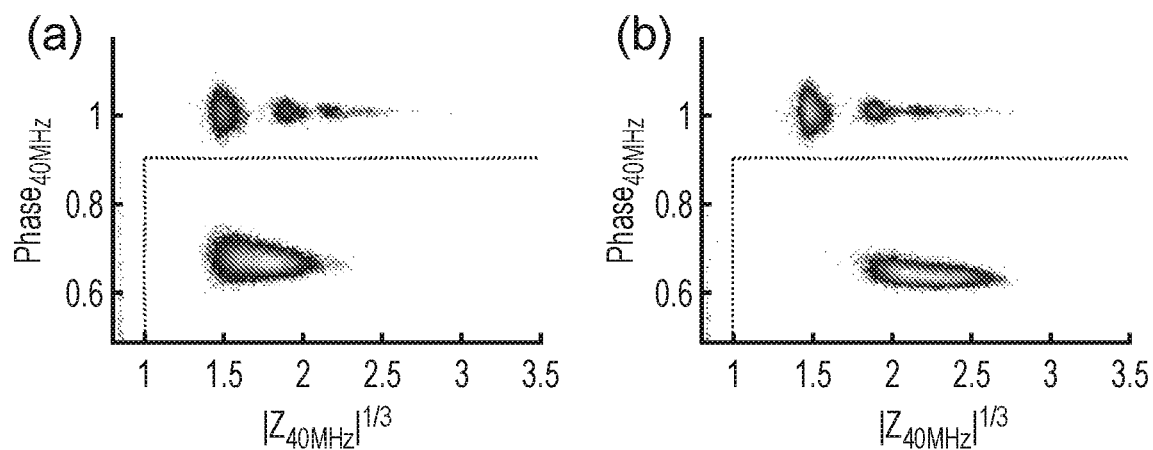
FIGS. 12 (a) and (b) show example scatter plots of impedance magnitude and phase data recorded from bacterial cell samples at one frequency with an impedance flow cytometry method according to an example of the present disclosure.

FIG. 12 shows two further example scatter plots, of data obtained at a high frequency of 40 MHz only. The x-axis of each graph plots the electric radius (cube root of the impedance magnitude) measured at 40 MHz. The y-axis of each graph plots the phase of the impedance signal measured at 40 MHz. As before, plastic microbeads were included in the samples; these appear at a phase value of about 1. Data points at lower phase values, around 0.7, indicate bacteria; hence phase measurements can readily distinguish between bacteria and beads. FIG. 12(a) shows a plot for a sample of bacteria that has not been treated with antimicrobial. The measured electric radii for the population range from about 1.5 to 2.1. FIG. 12(b) shows a plot for a sample of the same bacteria that have been exposed to an antimicrobial agent. The bacteria population has shifted to higher x-axis values, covering a range from about 1.8 to 2.7. Since it is known that exposure to an effective antimicrobial agent can alter bacterial cell size, we deduce that the bacterial strain is susceptible to the antimicrobial that has been applied.

Note that, in line with the ability to readily distinguish populations of bacteria from populations of beads by looking at the phase values, phase can also be used to distinguish between, or identify the presence of, populations or sub-populations (groups or sub-groups) of different microorganisms within one sample, if the different microorganisms have a different size and/or shape and/or morphology. The different microorganisms may by originally present in the sample, or may arise from an effect of the antimicrobial agent. For example, some agents change cell size with the effect of generating subpopulations of larger, smaller and intermediate persister cells.

Figure 13:
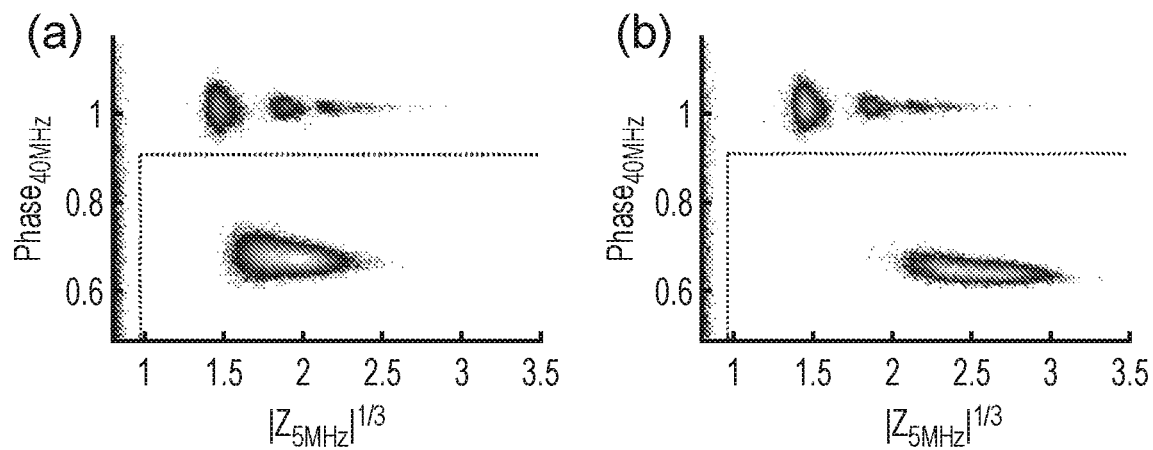
FIGS. 13 (a) and (b) show example scatter plots of impedance magnitude and phase data recorded from bacterial cell samples at two frequencies with an impedance flow cytometry method according to an example of the present disclosure.

As a further alternative, phase and magnitude values of the impedance at different frequencies may be combined. FIG. 13 shows further example scatter plots for data obtained at 5 MHz and 40 MHz. As for the FIG. 12 graphs, the FIG. 13 graphs plot the phase at 40 MHz on the y-axis. The x-axis, however, shows the electric radius at the low frequency, 5 MHz. FIG. 13(a) shows measurements from a sample of bacteria untreated with an antimicrobial agent, and FIG. 13(b) shows measurements from a sample of the same bacteria that has been treated with an antimicrobial agent to which the bacteria are susceptible. The bacteria and the antimicrobial agent are the same as for the FIG. 12 data. Both samples contained reference beads, having a phase value around 1. As with the FIG. 12 data, the bacteria are easily distinguished from the beads, having a lower phase value around 0.7. Note that the phase values are the same as in FIG. 12, since the phase data is obtained for the same, high, frequency. Again as before, the treated bacteria show a shift to larger values of electric radius, arising from the susceptibility to the antimicrobial agent causing an increase in cell size. Note that in this example, the apparent increase in cell size is greater than in FIG. 12, to values in the range of about 2.1 to 3. This is owing to the greater sensitivity of cell size to low frequency measurements than high frequency measurements.

From these results, it may be appreciated that a method according to the present disclosure may be used to apply electric signals (voltages or currents) to the first and second signal electrodes at one frequency, or at more than one frequency. Accordingly, an apparatus used to carry out the method may comprise one or more electrical signal sources operable to generate one frequency, or two or more frequencies. The one frequency may a high frequency, or a low frequency. The two or more frequencies may comprise two frequencies, one high and one low. A high frequency may be in range of about 10 MHz or above, such as between 10 and 1000 MHz, for example 40 MHz. In some applications, even larger frequencies may be useful, such as frequencies up to about 10 GHz. The low frequency is smaller than the high frequency and may be in the range of 10 MHz or below, such as between 1 and 10 MHz, for example 5 MHz. Other and/or additional frequencies are not precluded, however, and can be chosen with reference to a particular application. Similarly, the ratio between the low frequency and the high frequency can vary greatly depending on the application.

As described above, for example with respect to FIGS. 10, 11, 12 and 13, a method in accordance with the present disclosure can comprise obtaining a measurement from a sample of microorganisms that have been exposed to a selected antimicrobial agent (where the microorganisms are particles suspended in an electrolyte to provide a fluid that is passed through an arrangement of electrodes as described herein to obtain a differential signal and optionally an impedance signal derived from the differential signal) and another measurement from a sample of the same microorganism that have not been exposed to any antimicrobial agent, and comparing the two measurements. The unexposed microorganism population is used as a reference to which the exposed population is compared. Significant differences between the two measurements can indicate that the microorganisms are susceptible to the selected antimicrobial agent. The measurements can be arranged in scatter plots of data points corresponding to individual microorganisms, and the difference assessed by reference to a contour line around the population of unexposed microorganisms. A threshold value may be set, for example, so that if the antimicrobial exposure causes the number or the proportion of exposed microorganisms captured within the contour line to fall below the threshold, susceptibility is deduced. To obtain the two samples, a group of bacteria may be divided in half, before or after suspension in the electrolyte; one half is incubated with the antimicrobial agent and the other without antimicrobial agent, for a set period of time, such as 30 minutes. Then, the reference plastic beads can be added if desired, and both samples passed through an apparatus as described to obtain a differential signal from which impedance data can be derived.

However, it can be more useful to quantify antimicrobial susceptibility in more detail. In practice, susceptibility is more commonly defined as whether a microorganism strain is susceptible or resistant to a given concentration of antimicrobial agent. At very high concentrations, most antimicrobial agents will overcome microorganisms, but such high concentrations may not be safely or practically achievable in the human body. Under this approach, one can define a minimum inhibitory concentration, or MIC, which is the lowest concentration considered to have a noticeable inhibitory effect on the microorganism strain's population. Then, one can decide if the MIC is achievable in the human body, and hence if that particular antimicrobial agent can be used to combat infection caused by the particular microorganism. Therefore, it is useful to be able to measure the response of microorganisms to a range of different concentrations of an antimicrobial agent in order to determine the MIC. Methods according to the present disclosure are well-suited to enable this determination owing to their simplicity.

A method in line with the description thus far can be extended by dividing a sample of microorganisms into more than two groups, and exposing each group to a different concentration of antimicrobial agent, including an unexposed group to act as a reference sample, as before. In this way a MIC can be determined, or a previously-established value for the MIC can be verified or re-tested. To assess a MIC, groups or populations of microorganisms at similar concentrations are incubated with a range of antimicrobial concentrations, which are usually a control or reference concentration of 0, a concentration considered to be a clinically relevant MIC, and two or more concentrations (or dilutions) on either side of the MIC. Hence, the sample of microorganisms is divided into six groups, each of which undergoes an impedance measurement.

As an example, the microorganism sample for performing MIC assessment may comprise picking a colony of microorganisms from a plate and incubating the colony overnight in suitable media, such as trypticase soy broth (TSB) to produce a culture. An aliquot of the culture is diluted into Mueller Hinton broth (MHB) to a concentration of $5 \times 10^5$ cells/mL and incubated at 37° C. for 30 minutes to obtain an actively dividing culture. Aliquots (950 µL) of the actively dividing culture are added to each of seven prewarmed test tubes each containing 50 μL of MHB and a dose of antimicrobial, such as the antibiotic meropenem, to give a set of final antimicrobial concentrations of 0, 0.25, 0.5, 1, 2, 4 and 8 mg/L. The tubes are incubated for 30 minutes (antibiotic exposure), then washed once in Hanks balanced salt solution (HBSS) and subsequently diluted 1:10 in HBSS. 1.5 μm diameter reference beads are added to each sample ($10^4$/mL) Impedance flow cytometry measurements can then be carried out as described above, for example by using a syringe to introduce the sample into the cytometer apparatus at a rate of 30 μL/min for 3 minutes.

Figure 14:
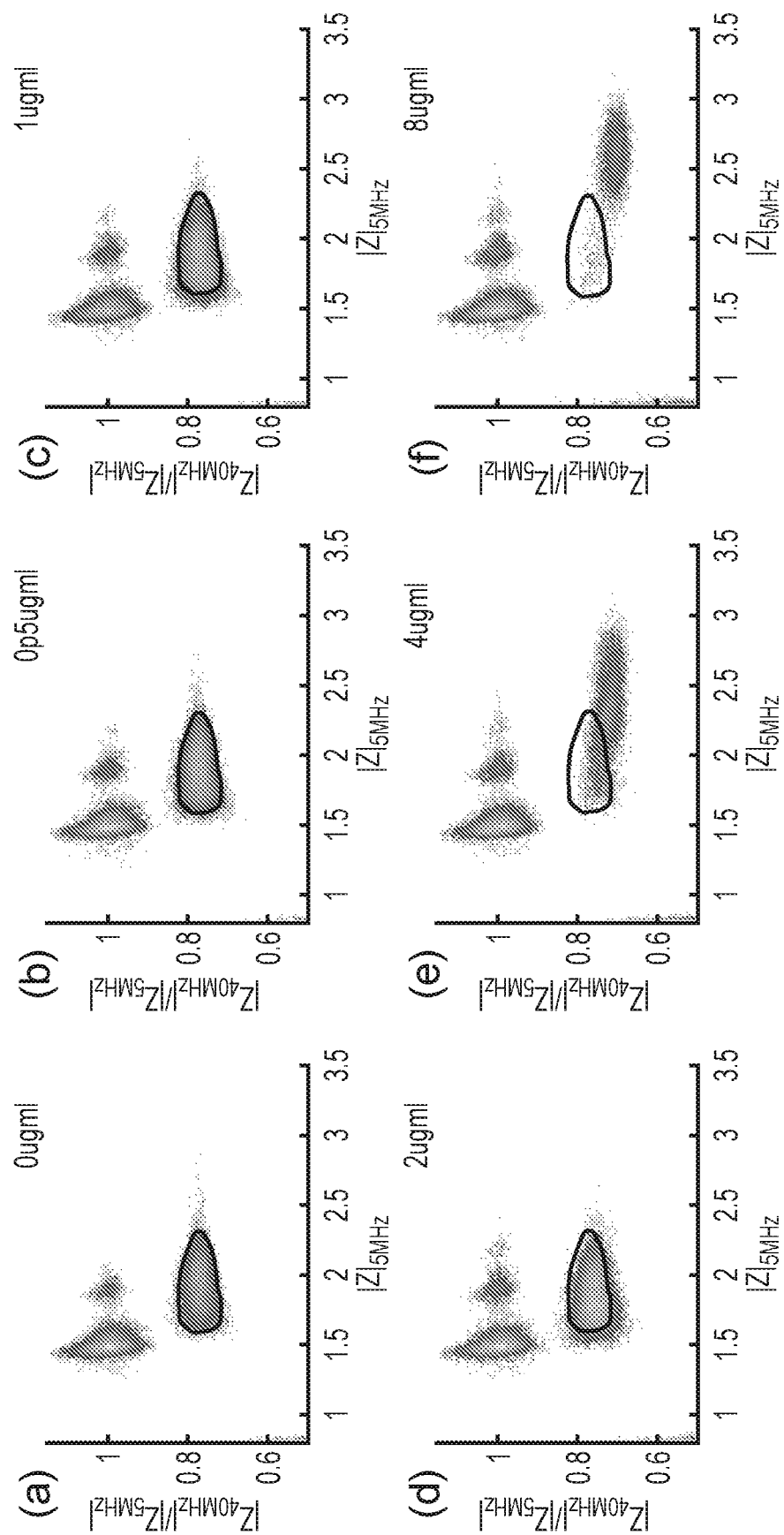
FIGS. 14 (a) to (f) shows example scatter plots of impedance data recorded from bacterial cell samples at two frequencies with an impedance flow cytometry method according to an example of the present disclosure, showing an effect of different concentrations of antimicrobial concentrations on a susceptible bacteria strain.

FIG. 14 shows six scatter plots of impedance measurements from six groups of bacteria exposed to a series of six antimicrobial concentrations. In this example, the concentrations were 0 μg/mL (control), and 0.5, 1, 2, 4 and 8 μg/mL as indicated on the graphs, where 2 μg/mL is the known, pre-defined MIC of the antimicrobial agent for the bacteria being tested. FIG. 14(a) shows the control or reference population not exposed to the antimicrobial agent, with the gating contour drawn around the bacteria population to encompass the majority of the data points. For the lower antimicrobial concentrations (FIGS. 14(b)-(d)), the bacteria can be seen to be resistant, since the data points are not moved out of the contour. Only at concentrations of 4 and 8 μg/mL is a significant shift out of the contour observed (FIGS. 10(e) and (f)). For these measurements, the data was obtained at two frequencies, a low frequency of 5 MHz and a high frequency of 40 MHz. The impedance value for each cell at the low frequency, $|Z|_{5\ MHz}$, is plotted on the x-axis, and the normalised impedance value for each cell at the high frequency, $|Z|_{40\ MHz}/|Z|_{5\ MHz}$, is plotted on the y-axis.

As discussed, the measured "shift" in biophysical properties arising from exposure to an antimicrobial agent to which a microorganism strain lacks resistance, and discernible as a change in the cell count inside a contour marking a distribution of impedance measurements from an unexposed population, may be quantified in a number of different ways, including a change in cell size, a change in cell wall/membrane properties, and/or a decrease in cell count, or a combination of these.

Figure 15:
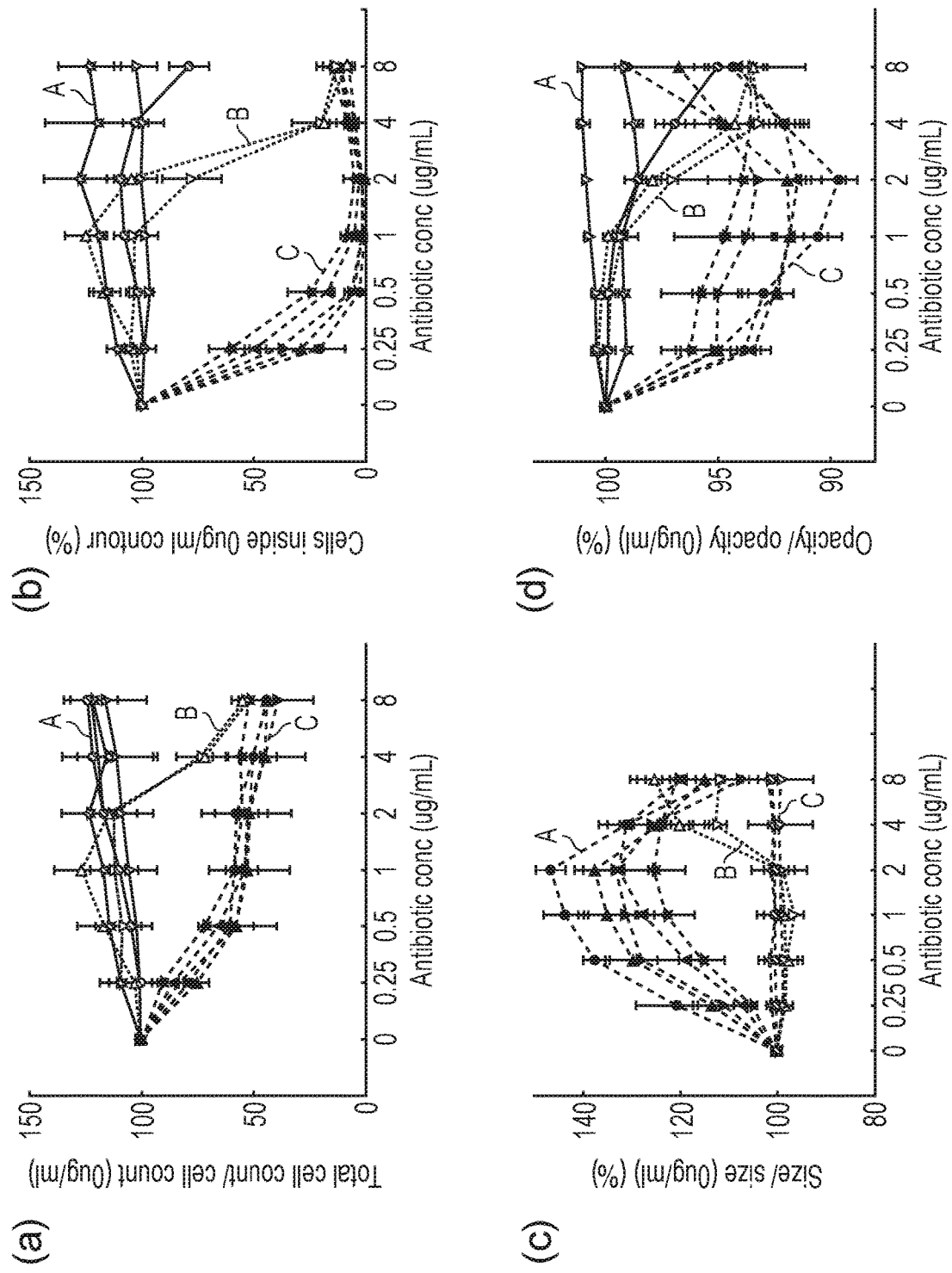
FIGS. 15(a) to (d) shows graphs of the variation of several bacteria cell characteristics with concentration of antimicrobial exposure, obtained with an impedance flow cytometry method according to an example of the present disclosure.

FIG. 15 shows graphs which summarise measurements of these properties for ten different strains of bacteria after exposure to different antimicrobial concentrations, where the values of the various properties are determined from impedance measurements obtained by methods according to the present disclosure. FIG. 15(a) shows the total cell count normalised to a reference cell count (y-axis) against antimicrobial concentration (x-axis). FIG. 15(b) shows the number of cells inside a contour gate normalised to a reference number (y-axis) against antimicrobial concentrations (x-axis) (and is hence similar to the total cell count in FIG. 15(a)). FIG. 15(c) shows the cell size normalised to a reference cell size (y-axis) against antimicrobial concentration (x-axis). FIG. 15(d) shows the opacity normalised to a reference opacity (y-axis) against antimicrobial concentration (x-axis). The group of lines A correspond to bacteria that are known to be highly resistant to the antimicrobial agent, so the properties are not affected much even at higher concentrations; the lines remain largely horizontal. The group of lines B show strains which are moderately resistant, so the properties are altered only at higher concentrations; the lines deviate from the horizontal at higher concentrations. The group of lines C shows strains which are known to be highly susceptible to the antimicrobial agent, so the properties are altered even at very low concentrations; the line deviate from the horizontal immediately the concentration exceeds zero. These four different graphs could be used separately or together to make a quantitative decision of the susceptibility of the bacteria. As an example, the total bacteria count in FIG. 15(a) for the C group is lower at 0.25 μg/mL (so the bacteria are susceptible at this concentration), but the lines of the B group only show a decrease in cell count at 4 μg/ml. A similar trend can be identified in the cell size shown in FIG. 15(c). A threshold could be defined to determine an appropriate MIC. For example, one could require that the cell size has to increase to 110% or above for the antimicrobial agent to be considered effective; the concentration that produces this change is taken as the MIC. Different antimicrobial agents and different microorganisms will have different profiles, resulting in different thresholds for the various properties to quantify the susceptibility and make a determination of susceptible or resistant for each isolate/antimicrobial agent concentration. The data could be analysed/correlated and/or calibrated against standard techniques for the measurement of susceptibility.

A drawback with the technique of optical cytometry is that the antimicrobial agent often has to be removed from a sample by a washing step before the necessary dye is added. This is because the dye can interfere with the growth of microorganisms. Hence the sample only captures the antimicrobial agent effect at the time of washing, and the optical measurement provides a "snapshot" only. This would prevent the study of the evolving effect of the antimicrobial agent over time without preparing a multiplicity of samples each washed after a different incubation time, which is both inconvenient, and expensive owing to the costly nature of the dyes. This latter point would make it expensive to assess MIC via optical cytometry owing to the need for a plurality of samples at different antimicrobial concentrations.

The methods of impedance flow cytometry described herein address this issue by enabling a continuous impedance measurement from a single microorganism sample, so that the evolution of the antimicrobial effect of an agent can be assessed. To achieve this, a single microorganism population is prepared in an electrolyte solution such as a growth medium as a fluid to be passed through an impedance measurement apparatus as described above, and an antimicrobial agent is applied to the microorganisms, and remains in the sample. The fluid, including the microorganisms and the antimicrobial agent, is passed into the apparatus flow channel promptly so that a first impedance measurement can be recorded soon after addition of the antimicrobial agent, for example within the first minute. On this time scale, the antimicrobial agent may not have a measurable effect on the microorganisms, so the microorganisms could be considered to be unexposed to the antimicrobial agent and this first measurement can be taken as a reference measurement corresponding to a measurement from an unexposed microorganism sample. The passage of the fluid through the flow channel is maintained at a constant rate, either by continuous extraction from a large sample, or by recirculation of fluid from a smaller sample, and multiple measurements are obtained, each at a specified time, for example, at intervals of one minute after the first, reference, measurement. Alternatively, measurements may be obtained on a continuous basis, and the results divided into data collected within successive time periods or bins, such as one minute intervals. Over the total measurement time, the antimicrobial agent continues to act on the microorganisms, and its effect over time can be determined by comparing the different measurements. The portions of the sample corresponding to each time interval can be considered as sub-samples, for each of which impedance measurements are gathered. In some cases, it may be desirable to add the antimicrobial agent to the sample after measurement on the sample has begun, if for example the antimicrobial agent acts quickly on the microorganism. This allows the first measurement to be a reference measurement from unexposed microorganisms. To achieve this, a single microorganism population can be prepared in an electrolyte solution such as a growth medium to obtain a fluid to be passed through an impedance measurement apparatus as described above. A measurement or multiple measurements are taken, and then the antimicrobial agent is added to the fluid. Measurements then continue on the exposed sample as described above.

Figure 16:
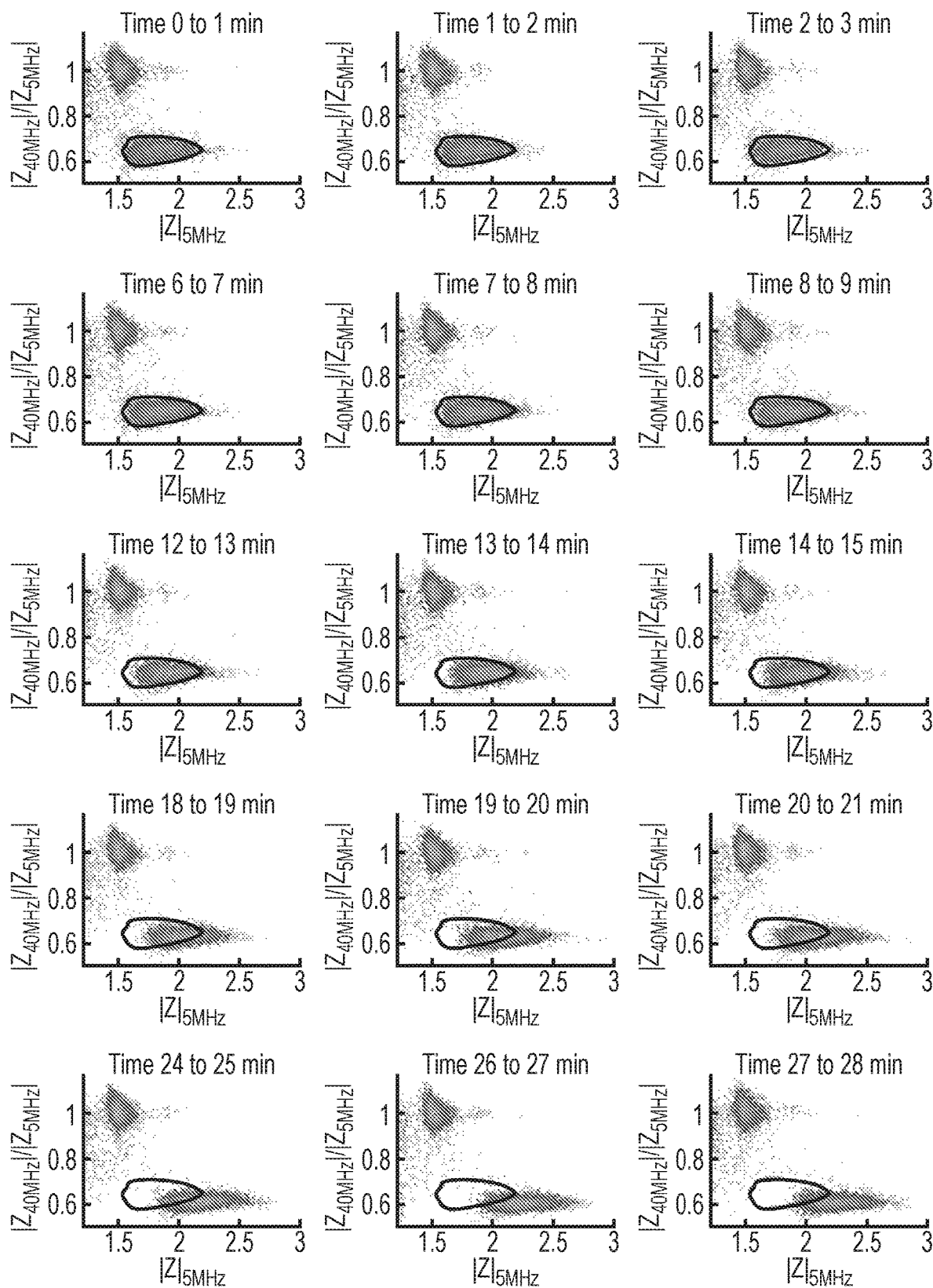
FIG. 16 shows a sequence of scatter plots of impedance data recorded continuously over time from a single sample of bacteria exposed to an antimicrobial agent using an impedance flow cytometry method according to an example of the present disclosure.
Figure 16:
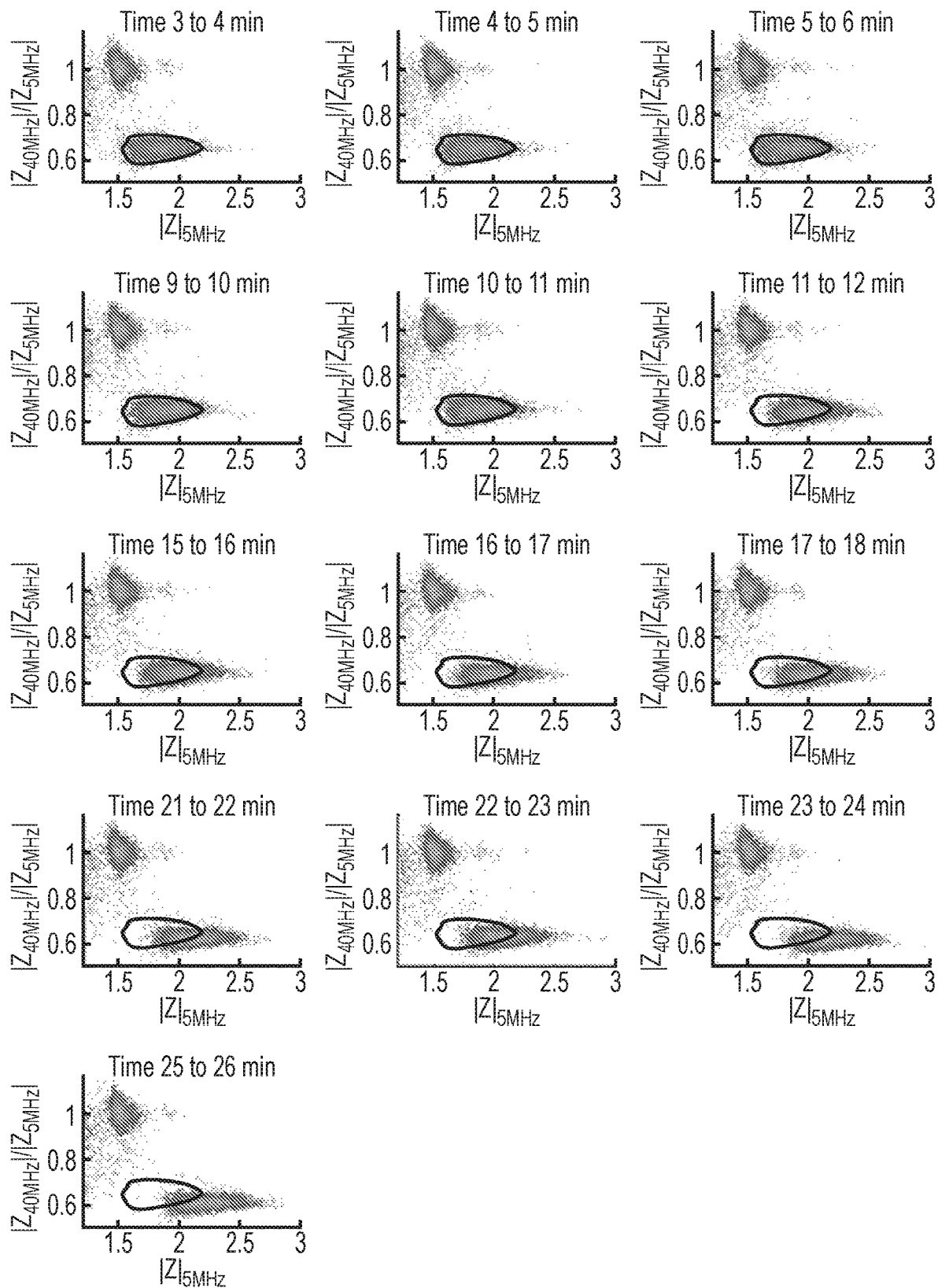

FIG. 16 shows a sequence of scatterplots of data obtained in this way, using a high frequency of 40 MHz and a low frequency of 5 MHz to obtain impedance measurements. A population of bacteria was exposed to antimicrobial agents and measured continuously over 26 minutes, and the resulting impedance data separated into bins corresponding to one minute intervals, and plotted on a graph. The sample fluid included plastic microbeads which appear as a population group in the upper left of each graph, as in previous examples. The upper left plot shows the data collected in the first minute (time of 0 to 1 minutes) which is designated as the reference or control data for unexposed bacteria. A contour line or gate is drawn around the unexposed bacteria population in this graph, and then replicated in each later graph so that alteration of the bacteria over time can be identified. A study of the sequence of graphs reveals that after about 15 minutes, the bacteria population starts to shift noticeably out of the contour line. Hence, we can deduce that the bacteria is susceptible to the particular antimicrobial agent. After 26 minutes, almost the whole population has moved out of the contour. Movement is to higher low frequency values, indicating an increase in cell size, and to a lesser extent to lower high frequency values, indicating that the antimicrobial agent also changes properties of the bacterial cell wall or its internal structure.

Figure 17:
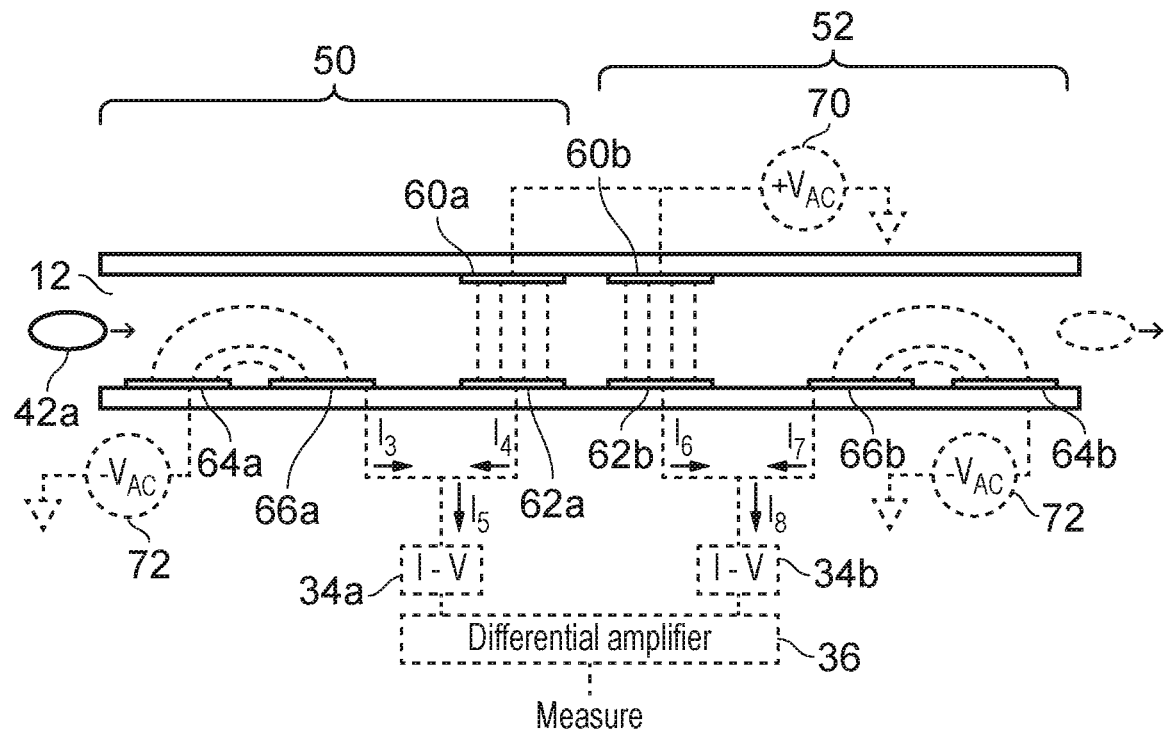
FIG. 17 shows a schematic cross-sectional side view of an electrode and circuitry configuration for an impedance flow cytometer according to an example with differently orientated current paths.

FIG. 17 shows a further example apparatus, with an alternative arrangement of electrodes. Eight electrodes are provided to define four current paths, in two groups each comprising a first current path and a second current path, as in some preceding examples. However, while preceding examples have comprised only one current path orientation within a single system, the FIG. 17 example includes two orientations of current path, which enables additional information to be determined about particles in a sample.

In particular, the apparatus is configured so that in each of the first electrode group 50 and the second electrode group 52, there is a current path which is substantially transverse to the fluid flow direction and a current path which is substantially parallel to the fluid flow direction. In the first electrode group 50, a first signal electrode 60a supplied with +V from a voltage source 70 is arranged above the channel, opposite to a first measurement electrode 62a below the channel, to define a first current path transverse to the flow direction, from which a current I4 is measured. A second signal electrode 64a supplied with −V from a voltage source 72 is arranged below the channel adjacent to a second measurement electrode 66a also below the channel, to define a second current path which is parallel to the flow direction, from which a current I3 is measured. As before, I3 and I4 are combined to produce a first summed signal I5, from the first electrode group 50. Similarly, in the second electrode group 52, a further first signal electrode 60b is opposite to a further first measurement electrode 62b to define a transverse first current path I6, and a further second signal electrode 64b is adjacent to a further second measurement electrode 66b to define a parallel second current path I7. I6 and I7 are combined to generate the second summed signal I8, and as in previous examples, the summed signals are handled by current to voltage converters 34a, 34b and a differential amplifier 36 to determine a differential signal.

The provision of differently oriented current paths along the same flow path can reveal information about particle shape. In the absence of any particle, the magnitudes of the various current paths are approximately equal, summing to approximately zero, as before. In the presence of a spherical or near-spherical particle, as described with respect to FIGS. 1 to 9, the impedance signals measured for transverse current paths have approximately the same magnitude as the impedance signals measured for parallel current paths. However, if a particle 42a is non-spherical, such as an elongate rod-shaped bacteria (for example a *Bacillus*), it will interact by different amounts with the two current path directions, giving differently-sized signals. If the elongate particle has its longest axis arranged along the channel flow direction, it will produce a larger change in the transverse current path than in the parallel current path. Accordingly, the summed signal derived from the two current paths within an electrode group will be different for an elongate particle compared to a spherical particle, the difference being related to the degree by which the particle shape differs from a sphere (in other words, its degree of eccentricity or elongation). Therefore, obtaining the summed signals from current paths of two different orientations (such as a transverse path and a parallel path) provides a differential signal that can indicate information about particle eccentricity or shape. This is useful for distinguishing between different types of bacteria, such as bacilli (rods) and cocci (spheres), or identifying chains of bacteria. Additionally it can be used to enhance the measurement of AST by identifying particles that have been arrested during the division cycle, as is the case for treatment with β-lactam antimicrobial agent. It is known for example that treatment of cells with different concentrations of β-lactam antimicrobial agents leads to different and distinct morphological forms. Antimicrobial agents acting at an early block point give dumbbell shapes whereas those affecting at a later time give lemon-shaped cells [2].

The external shape of a particle can reveal other properties. For example, if the flow of the sample fluid through the cytometer channel creates sufficient shear stress, a cell can be deformed or squashed as it travels along the channel. Softer cells will be deformed more than stiffer cells, acquiring a greater degree of eccentricity. Accordingly, an arrangement as in the FIG. 17 example that uses current paths of different orientations to detect cell eccentricity, can additionally be used to distinguish or determine mechanical properties of particles. A softer particle will produce different summed signals and differential signal than a stiffer particle, owing to the different shape induced by the flow. The action of an antimicrobial agent on a microorganism species may also produce changes in mechanical properties.

Note that the electrodes might be positioned to provide the two orientations of current path in a different order along the flow direction than that shown in FIG. 17.

Figure 18:
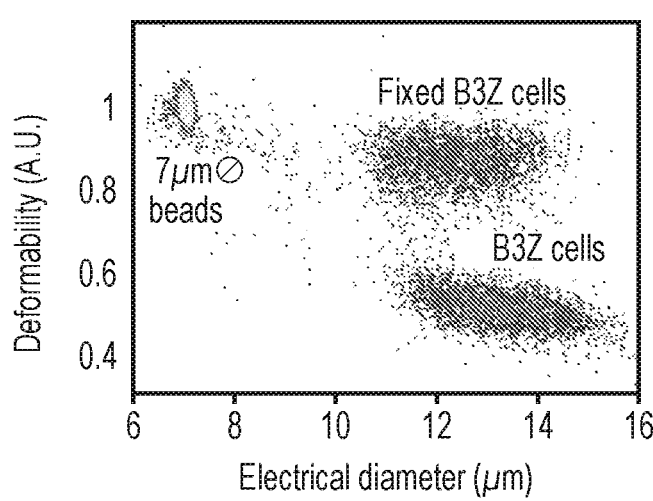
FIG. 18 shows an example scatter plot of impedance magnitude data obtained using an impedance flow cytometry method in an apparatus such as the FIG. 17 example.

FIG. 18 shows a scatterplot of impedance data obtained from two different cell types. As before, each data point represents a single particle in a sample. The vertical axis shows a "deformability" measure, obtained by dividing the impedance measurement from one or more parallel current paths by the impedance measurement from one or more transverse current paths. The horizontal axis indicates the electrical diameter of the particles, obtained by averaging the impedance signals from the two measurement directions, which approximates cell size. Alternatively, the diameter might be obtained in line with the measurement of electrical radius discussed with regard to FIG. 12. Measurements were obtained for two groups of B3Z cells, which have a spherical shape. One group was modified by a fixing treatment with glutaraldehyde to increase the membrane stiffness. Note that the measurement could be made on a single sample containing both groups of cells, or on two samples, each containing one group. The cells in the two groups therefore have different mechanical properties, and appear on the scatterplot as two well-separated populations. Measurements of a reference population of 7 μm beads is also indicated. The stiffer, fixed cells remain substantially spherical in the fluid flow along the channel, so the impedance signals measured for the two orthogonal current paths are similar. Hence the deformability for these cells is measured as near to 1 arbitrary unit. In contrast, the unfixed cells are deformed by the flow and stretch out along the channel direction. Accordingly, the impedance signals measured along the channel direction are reduced compared to the measurements across the channel, and the deformability measure is reduced below 1 AU. In this example, it is measured at about 0.5 AU. Thus, mechanical properties of individual cells and populations of cells can be identified, and different cell populations can be distinguished one from another.

The technique of assessing antimicrobial susceptibility by determining the minimum inhibitory concentration (MIC) has been described above, together with an indication of how to carry this out using the described impedance flow cytometry methods. An alternative technique is that of breakpoint analysis, in which bacteria samples are exposed to one or two concentrations of antimicrobial (antibiotic) and classified as susceptible/not susceptible (S/NS), resistant/not resistant (R/NR), or of intermediate resistance, depending on the response of the samples to the antimicrobial. The response can be measured using the described impedance flow cytometry.

In breakpoint analysis, bacteria are assessed at one or two pre-defined concentrations of antibiotic that are tabulated by standards institutes such as the Clinical & Laboratory Standards Institute (CLSI) in the USA and the European Committee on Antimicrobial Susceptibility Testing (EUCAST). To preform the analysis, bacteria growth is assessed at a first concentration X, which sets a boundary for S/NS. If the bacteria do not grow (i.e. the number of bacteria in the tested sample does not increase) they are classified as susceptible to the antibiotic. If the bacteria grow, they are classified as not susceptible to the antibiotic. Additionally, growth of the bacteria can be assessed at a second concentration Y, which is higher than concentration X and sets a boundary of R/NR. If the bacteria grow, they are classified as resistant to the antibiotic; if they do not grow, they are classified as not resistant. The values of concentration X and concentration Y depend on the strain of bacteria and the type of antibiotic. Some strains of bacteria may grow at concentration X (or higher) but not at concentration Y; these are classified as not resistant but also not susceptible, a characteristic commonly termed as intermediate resistance. For some antibiotics and some bacteria species, there is no intermediate region, in other words, concentration X and concentration Y are equal, and testing at only one concentration is required. In either case, a sample of bacteria that has not been exposed to the antibiotic is also tested using the impedance flow cytometry in order to obtain the reference population gate or contour described above.

As a non-limiting example, samples for impedance flow cytometry-based breakpoint analysis can be prepared in the following manner. Three colonies of bacteria are selected from a plate, and added to 3 mL of MHB. This sample is vortexed to resuspend the bacteria in the broth, and then diluted to a concentration of $5 \times 10^5$ cells/mL in MHB. The sample is then incubated for thirty minutes to obtain an actively dividing culture. Aliquots of 500 μL are added to test tubes containing 500 μL of pre-warmed MHB each with a final antibiotic concentration at the clinical breakpoint (S/NS and/or R/NR), for example according to current EUCAST guidelines. These might be 2 mg/L (S/NS) and 16 mg/L (R/NR) for the antibiotic meropenem, or 1 mg/L for ciprofloxacin, or 8 mg/L for gentamicin, or 4 mg/L for colistin, or 8 mg/L for ceftazidime, amoxicillin/clavulanic acid and cefoxitin, along with a control sample at 0 mg/L. Each tube is incubated for thirty minutes (antibiotic exposure) before the sample are diluted at a level of 1:10 in HBSS, and 1.5 μm reference beads are added. The samples can then be passed through an impedance flow cytometry apparatus at a rate of 30 μL/min for a measurement period of 2 minutes.

Figure 19:
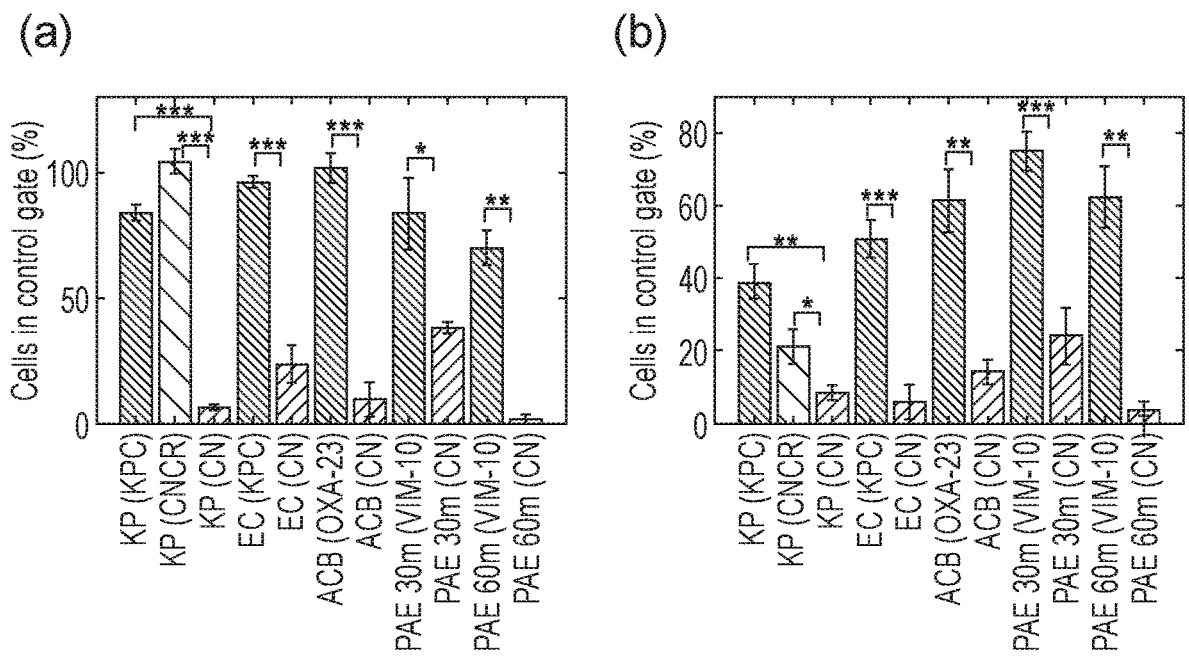
FIG. 19 shows bar charts of bacterial cell populations treated with antibiotics at concentrations predefined for breakpoint analysis of susceptibility and resistance, measured using impedance flow cytometry.

FIG. 19 shows bar charts of example data measured using impedance flow cytometry to perform breakpoint analysis. Eleven different strains of bacteria were exposed to the antibiotic meropenum. The charts show, for each strain, the percentage of the bacterial population remaining in the reference gate or contour (measured for an unexposed sample of the bacteria) after exposure to the antibiotic. FIG. 19(a) shows data for the susceptible/not susceptible (S/NS) breakpoint, for which the antibiotic concentration is 2 mg/L and FIG. 19(b) shows data for the resistant/not resistant (R/NR) breakpoint, for which the antibiotic concentration is 16 mg/L. The bacteria are labelled as KP (*Klebsiella pneumonia*), EC (*Esch coli*), ACB (*Acinetobacter baumannii*) and PAE (*Pseudomonas aeruginosa*). The bars show a mean value±the standard deviation (N=3; *$p<0.05$; $p<0.01$; *$p<0.001$ with p-values obtained using the Student's t-test for independent samples (one tailed)). The shading of the bars represents susceptibility and resistance determined by the conventional technique of broth microdilution, where the densest shading indicates resistant strains and intermediate shading indicates susceptible strains. There is good correspondence between these designations and the measured percentage of cells in the control gate, indicating impedance flow cytometry is an accurate technique for performing breakpoint analysis. The least densely shaded bar in each chart is for KP (CNCR) which is a carbapenemase negative strain of KP that is resistant to carbapenems.

Figure 20:
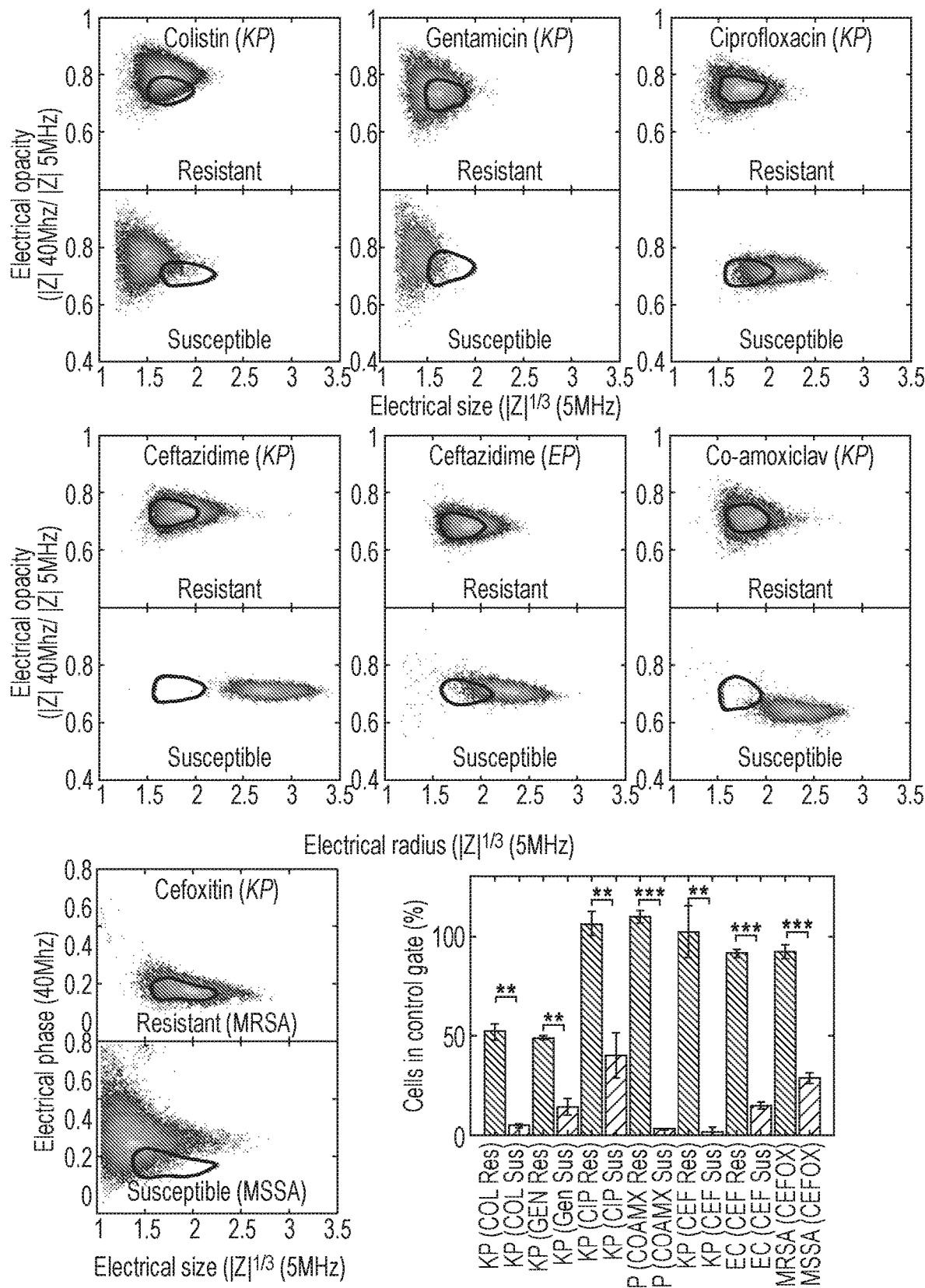
FIG. 20 shows scatter plots of impedance data recorded from a variety of bacterial cell samples exposed to various antibiotics at predefined breakpoint analysis concentrations together with a bar chart of the corresponding cell populations of each sample.

FIG. 20 shows a set of scatter plots of data obtained using impedance flow cytometry for resistant and susceptible strains of three bacteria, *Klebsiella pneumonia* (KP), *Escherichia coli* (EC), and *Staphylococcus aureus* (SA) exposed to different antibiotics, indicated in the heading of each scatter plot. The various antibiotics have different mechanisms of action to alter the cell size, shape, structure and/or count, leading to different impedance responses which can be detected by the impedance flow cytometry. This can be appreciated from the various different movements of the data points indicating the cell populations relative to the gate contours. The resistant bacteria are unaffected by the antibiotics, so the populations remain within the gate contours. The susceptible bacteria are affected by the antibiotics, so the populations are altered with respect to the size, shape and position of the gate contours. The antibiotic concentrations were at the R/NR breakpoint concentrations for the various bacteria strain/antibiotic combination.

The scatter plots for the antibiotics Colistin, Gentamicin, Ciprofloxacin, Ceftazidime and Co-amoxiclav are shown as electric cell size or radius (being the cube root of the measured low frequency (5 MHz) impedance as explained above) against electrical opacity (being the measured high frequency impedance (40 MHz) normalised to the low frequency impedance as explained above). The scatter plot for Cefoxitin is shown as electric cell size against the measured high frequency (40 MHz) phase impedance because this measure gives a clearer difference between resistant and susceptible for the particular antibiotic mechanism of Cefoxitin.

Also included in FIG. 20 is a bar chart similar to those of FIG. 19, showing the percentage of cells remaining in the gate contour for each bacteria/antibiotic combination. Again, the denser shading and the less dense shading correspond respectively to resistance and susceptibility determined by conventional broth microdilution, to show that comparable results are obtainable using impedance flow cytometry.

Impedance flow cytometry methods according to the examples and embodiments herein offer a number of benefits. Testing and measurements can be carried out quickly and with an improved sensitivity, particularly for smaller particles such as bacteria so the methods are valuable for AST and other microorganism assays. Apparatus suitable for performing the methods can be compact, potentially portable, and inexpensive, such as a chip-based format which lends itself to mass production, and scalability for multiple simultaneous tests. In the context of testing microorganism susceptibility to antimicrobial agents, tests can be prompt and simple, and inexpensive since no dye or other labelling medium is required. This also enables continuous monitoring of the response of any given sample to antimicrobial agents over an extended time period, which is not typically possible in dye-based testing procedures such as optical cytometry.

As an example of the improved speed of testing offered by impedance flow cytometry, consider the case of a patient on an intensive care ward who presents with a urinary tract infection and is immediately prescribed the antibiotic co-amoxiclav as the conventional standard to care for this condition. The patient sample is sent for testing within the hospital microbiology unit and after an overnight culture of the bacteria taking 16 hours from collection of the sample, the isolate is identified as E. coli using, for example, a Biotyper system manufactured by Bruker, which takes another 2 hours or so. This identification can lead to a change in antibiotic to a type considered more suitable, followed a further period of a day or so in which observation of the patient indicates whether the bacteria is resistant to the antibiotic, in which a further change of antibiotic. In contrast, rapid AST using an impedance flow cytometer performed at the 16 hour mark with one or more antibiotic types can identify an antibiotic to which the bacteria is susceptible in a period of just 30 minutes, so that the prescription can be optimised. For example, it may be found that the E. coli strain is resistant to co-amoxiclav, but susceptible to meropenem.

Methods described herein may be used to measure and analyse particles of non-biological origin, so examples may be considered more generally as particle impedance measurement methods, which may be performed using apparatus configured (for example as regards its dimensions) for use with biological particles (in particular cells which may or may not be bacteria) or non-biological particles, or any particle type. The terms "impedance flow cytometry", "impedance flow cytometry method", "impedance flow cytometer" and "impedance flow cytometry apparatus" are intended to cover any method and apparatus as described herein regardless of the nature of the particles, although in some examples the particle type is relevant, such as impedance flow cytometry for AST and MIC determination. The disclosure is not limited in this regard.

The impedance flow cytometry can be used to measure the electrical (impedance) properties of bacteria without any dyes. The technique can directly measure the phenotypic response of an organism and does not require incubation with a dye. Furthermore, the technology can be carried out on compact and scalable apparatus, so that several measurements can be made in parallel using a custom design of chip with multiple channels. The electrical properties can be measured continuously as a function of time to determine the evolution of the response to antimicrobials. This is not usually done using dyes as they are washed away prior to measurements.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilised and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in the future.

REFERENCES

[1] WO 2012/164547
[2] M J Pucci et al, "Inhibition of beta-lactam antibiotics at two different times in the cell cycle of Streptococcus faecium ATCC 9790", Bacteriology 165 682-688, 1986

The invention claimed is:
1. A method of antimicrobial agent susceptibility testing comprising:
preparing samples of microorganisms suspended in an electrolyte, comprising a first sample of the microorganisms unexposed to antimicrobial agents and a second sample of the microorganisms exposed to an antimicrobial agent;
adding non-biological particles to each sample;
passing the first sample through an impedance flow cytometer to obtain a first impedance signal representing one or more components of impedance values of the unexposed microorganisms;
passing the second sample through the impedance flow cytometer to obtain a second impedance signal representing one or more components of impedance values of the microorganisms exposed to the antimicrobial agent;
comparing the first impedance signal and the second impedance signal; and determining a susceptibility of the microorganisms to the antimicrobial agent based on any differences between the first impedance signal and second impedance signal.

2. A method according to claim 1, further comprising preparing additional samples of the microorganisms each exposed to a different concentration of the antimicrobial agent;
passing each additional sample through the impedance flow cytometer to obtain a corresponding additional impedance signal;
comparing each additional impedance signal with the first impedance signal; and
determining a minimum concentration of the antimicrobial agent to which the microorganisms are susceptible based on any differences between the first impedance signal and the second and additional impedance signals.

3. A method according to claim 1, in which preparing the samples of microorganisms comprises including the microorganisms for the first sample, the second sample and any additional samples in a volume of electrolyte to produce a single sample and adding the antimicrobial agent to the single sample; and the method comprising:
passing the single sample through the impedance flow cytometer;
obtaining impedance signals for the single sample at two or more time intervals during passage of the single sample through the impedance flow cytometer, wherein an impedance signal at a first time interval is the first impedance signal, an impedance signal at a second time interval is the second impedance signal; and impedance signals at later time intervals are additional impedance signals; and
including the additional impedance signals in the comparing and the determining, such that the determining is based on any differences between the first impedance signal, the second impedance signal and the additional impedance signals.

4. A method according to claim 1, in which preparing the samples of microorganisms comprises including the microorganisms for the first sample, the second sample and any additional samples in a volume of electrolyte to produce a single sample; and the method comprising:
passing the single sample through the impedance flow cytometer;
obtaining the first impedance signal in a first time interval during passage of the single sample through the impedance flow cytometer;
adding an antimicrobial agent to the single sample after the first time interval; and
obtaining further impedance signals in one or more additional time intervals during passage of the single sample through the impedance flow cytometer, wherein an impedance signal in a second time interval after the first time interval is the second impedance signal and impedance signals in later time intervals are additional impedance signals; and
including the additional impedance signals in the comparing and the determining, such that the determining is based on any differences between the first impedance signal, the second impedance signal and the additional impedance signals.

5. A method according to claim 1, in which the second sample comprises the microorganisms exposed to a concentration of the antimicrobial agent predefined for use in breakpoint analysis of the microorganisms, and the determining a susceptibility comprises classifying the microorganisms as susceptible, not susceptible, resistant, or not resistant to the antimicrobial agent.

6. A method according to claim 5, in which the concentration of the antimicrobial agent in the second sample is a concentration predefined to indicate that the microorganisms are susceptible or not susceptible to the antimicrobial agent, and the method further comprises:
preparing a third sample of the microorganisms exposed to the antimicrobial agent at a higher concentration than the second sample which is predefined to indicate that the microorganisms are resistant or not resistant to the antimicrobial agent;
passing the third sample through the impedance flow cytometer to obtain a third impedance signal representing one or more components of impedance values of the microorganisms exposed to the antimicrobial agent;
comparing the first impedance signal and the third impedance signal; and
the determining a susceptibility comprises classifying the microorganisms as susceptible or not susceptible based on any differences between the first impedance signal and the second impedance signal, and classifying the microorganisms as resistant or not resistant based on any differences between the first impedance signal and the third impedance signal.

7. A method according to claim 1, in which the components of the impedance values of the unexposed microorganisms and/or of the microorganisms exposed to the antimicrobial agent indicate one or more of microorganism size, microorganism shape, microorganism cell wall structure, cell membrane properties and microorganism internal structure.

8. A method according to claim 1, comprising obtaining the impedance signals using current paths arranged along more than one direction relative to a direction of passage of the sample through the impedance flow cytometer so that the impedance values of the unexposed microorganisms and/or of the microorganisms exposed to the antimicrobial agent indicate a shape of the microorganisms.

9. A method according to claim 1, comprising obtaining the impedance signals using current paths arranged along more than one direction relative to a direction of sample passage through the impedance flow cytometer, and further comprising deducing a stiffness of the microorganisms by comparing impedance signals obtained using current paths with different directions.

10. A method according to claim 1, comprising obtaining the impedance signals at more than one frequency.

11. A method according to claim 1, in which the non-biological particles comprise reference beads.

12. A method according to claim 11, in which the reference beads are of known size and/or concentration.

13. A method according to claim 11, in which the reference beads provide reference information in the impedance signals for use in compensating fluctuations in the samples and/or in operation of the impedance flow cytometer.

14. A method according to claim 13, comprising determining phase and/or magnitude of the impedance signals in order to distinguish between the microorganisms and the non-biological particles within the impedance signals, and/or between the microorganisms and any different microorganism species in the samples.

15. A method according to claim 14, further comprising using the phase and/or magnitude to improve the resolution of impedance signals obtained from the impedance flow cytometer.

* * * * *